US012507911B2

(12) United States Patent
Paul et al.

(10) Patent No.: US 12,507,911 B2
(45) Date of Patent: Dec. 30, 2025

(54) EXIT DETECTION SYSTEM WITH OBSTRUCTION REACTION

(71) Applicant: Stryker Corporation, Kalamazoo, MI (US)

(72) Inventors: Anish Paul, Portage, MI (US); Madhu Sandeep Thota, Portage, MI (US)

(73) Assignee: Stryker Corporation, Portage, MI (US)

( * ) Notice: Subject to any disclaimer, the term of this patent is extended or adjusted under 35 U.S.C. 154(b) by 458 days.

(21) Appl. No.: 18/008,864

(22) PCT Filed: Sep. 28, 2021

(86) PCT No.: PCT/US2021/052390
§ 371 (c)(1),
(2) Date: Dec. 7, 2022

(87) PCT Pub. No.: WO2022/072340
PCT Pub. Date: Apr. 7, 2022

(65) Prior Publication Data

US 2023/0233102 A1 Jul. 27, 2023

Related U.S. Application Data

(60) Provisional application No. 63/085,523, filed on Sep. 30, 2020.

(51) Int. Cl.

| | |
|---|---|
| ***A61B 5/11*** | (2006.01) |
| ***A61B 5/00*** | (2006.01) |
| ***A61G 7/012*** | (2006.01) |

(52) U.S. Cl.
CPC .......... *A61B 5/1115* (2013.01); *A61B 5/0004* (2013.01); *A61B 5/6892* (2013.01);
(Continued)

(58) Field of Classification Search
CPC .......... A61G 7/00; A61G 7/012; A61G 7/015; A61G 7/018; A61B 5/00; A61B 5/0004;
(Continued)

(56) References Cited

U.S. PATENT DOCUMENTS

| | | | |
|---|---|---|---|
| 4,325,061 | A | 4/1982 | Wolar |
| 4,407,030 | A | 10/1983 | Elliott |

(Continued)

FOREIGN PATENT DOCUMENTS

| | | |
|---|---|---|
| EP | 854357 | 7/1998 |
| WO | 9705844 | 2/1997 |
| WO | 2021231674 | 11/2021 |

*Primary Examiner* — Van T Trieu

(74) *Attorney, Agent, or Firm* — Gardner, Linn, Burkhart & Ondersma LLP

(57) ABSTRACT

A person support apparatus, such as a bed, stretcher, cot, recliner, or the like, includes an exit detection system having a plurality of force sensors that support the weight of an occupant positioned on a support surface and obstruction detection system having one or more obstruction sensors. The force sensors are part of an exit detection system that issues an alarm when the occupant exits, or is about to exit, the person support apparatus. The bed exit system can react to detection of an obstacle. The distribution of weight applied to the force sensors is used to determine if the occupant is about to exit the person support apparatus. Compensation is made to the exit detection system for changes in the weight distribution that are not caused by movement of the occupant. Such changes may be due to not only movement of the person support apparatus or components thereof, but obstacles encountered by the person support apparatus or components thereof.

19 Claims, 10 Drawing Sheets

(52) U.S. Cl.
CPC ............ *A61B 5/7221* (2013.01); *A61B 5/746* (2013.01); *A61G 7/012* (2013.01); *A61G 2203/32* (2013.01)

(58) Field of Classification Search
CPC ......... A61B 5/11; A61B 5/1115; A47C 20/00; A47C 20/04; A47C 23/00
See application file for complete search history.

(56) References Cited

U.S. PATENT DOCUMENTS

| | | | | |
|---|---|---|---|---|
| 4,534,077 | A | 8/1985 | Martin | |
| 4,958,638 | A | 9/1990 | Sharpe et al. | |
| 5,276,432 | A | 1/1994 | Travis | |
| 5,317,769 | A | 6/1994 | Weismiller et al. | |
| 5,771,511 | A | 6/1998 | Kummer et al. | |
| 6,279,183 | B1 | 8/2001 | Kummer et al. | |
| 7,834,768 | B2 | 11/2010 | Dixon et al. | |
| 8,134,473 | B2 | 3/2012 | Roussy | |
| 8,502,663 | B2 | 8/2013 | Riley et al. | |
| 8,959,681 | B2 | 2/2015 | Richards | |
| 8,978,181 | B2 | 3/2015 | Menke et al. | |
| 9,009,893 | B2 | 4/2015 | Kramer et al. | |
| 9,655,796 | B2 | 5/2017 | Riley et al. | |
| 9,934,427 | B2 | 4/2018 | Derenne et al. | |
| 10,391,008 | B2 | 8/2019 | Zerhusen et al. | |
| 10,786,408 | B2 | 9/2020 | Sidhu et al. | |
| 11,020,297 | B2 | 6/2021 | Tessmer et al. | |
| 2015/0351982 | A1* | 12/2015 | Krenik .................. | A47C 23/06 5/616 |
| 2018/0325270 | A1* | 11/2018 | Purser .................. | A47C 20/041 |
| 2019/0183700 | A1 | 6/2019 | Roussy et al. | |
| 2019/0240094 | A1 | 8/2019 | Furman et al. | |
| 2021/0052197 | A1 | 2/2021 | Sukumaran et al. | |
| 2021/0338505 | A1 | 11/2021 | Nahavandi et al. | |
| 2021/0353179 | A1 | 11/2021 | Sukumaran et al. | |

* cited by examiner

EXIT DETECTION SYSTEM WITH OBSTRUCTION REACTION

CROSS-REFERENCE TO RELATED APPLICATIONS

This application claims priority to U.S. provisional patent application Ser. No. 63/085,523 filed Sep. 30, 2020, by inventors Anish Paul et al. and entitled EXIT DETECTION SYSTEM WITH OBSTRUCTION REACTION, the complete disclosure of which is incorporated herein by reference.

BACKGROUND

The present disclosure relates to person support apparatuses, such as beds, cots, stretchers, operating tables, recliners, or the like. More specifically, the present disclosure relates to person support apparatuses that include sensors for detecting obstacles and sensors for detecting when an occupant of the person support apparatus has exited therefrom, or may be about to exit therefrom.

Existing hospital beds and/or stretchers often include a bed exit system that is adapted to detect when a patient has exited the bed, or when a patient may be about to exit the bed. Typically, such beds include circuitry for providing an audio or visual alert when such an exit or pre-exit situation is detected. In many cases, the bed or stretchers include circuitry for transmitting a signal to a remote location, such as a nurses' station, so that the appropriate caregivers are notified of the exit, or pre-exit condition, and can respond appropriately. Existing exit detection systems often rely on an analysis of the outputs of multiple load cells. In some existing systems, the load cells outputs are monitored to compute a location of the occupant and if that location moves out of a defined area, an exit alert is issued. In other existing systems, the load cell outputs are monitored and one or more ratios of the forces detected by one or more of the load cells are computed. If the one or more ratios change by an amount greater than a threshold amount, an exit alert is issued.

SUMMARY OF THE INVENTION

According to various embodiments, the present disclosure provides an improved person support apparatus having an exit detection system that reacts to obstruction detection. The exit detection system can react by compensating for the obstruction, deactivating the bed exit system until the obstruction is removed, or by issuing an exit alert. By taking one or more of these actions, the improved person support apparatus is able to avoid situations where its exit detection system might otherwise experience an error, or generate an unreliable assessment of the patient's position and/or movement, due to the obstruction exerting forces on the force sensors of the exit detection system. That is, the forces exerted by the obstruction on the force sensors might otherwise be interpreted as forces due to patient movement, which could incorrectly lead to an exit alert being issued when such an alert is not correct, or which could incorrectly lead to no exit alert being issued when such an alert would be correct. The improved person support apparatus therefore helps overcome reliability issues with its exit detection system when an obstruction is encountered.

In some embodiments, the exit detection system may be configured to automatically attempt to compensate for errors introduced into its force sensor readings from the impact with an obstruction. In such embodiments, the compensation may include shifting a calculated center of gravity of the patient by an amount equal to the shift caused by contact with the obstruction, and/or it may involve changing a size, shape, and/or position of one or more zones in order account for the contact with the obstruction (in those embodiments wherein the exit detection system is configured to issue an alert when the calculated center of gravity goes outside one of the zones).

According to one embodiment of the present disclosure, a person support apparatus is provided that includes a litter frame, a lift system, a support deck, an obstruction sensor, an exit detection system, and a controller. The lift system is adapted to raise and lower a height of the litter frame. The support deck is supported on the litter frame and adapted to support thereon an occupant of the person support apparatus. The obstruction sensor is adapted to detect when the litter frame contacts an obstruction during movement of the litter frame. The exit detection system is adapted to be in an armed state and a disarmed state. When in the armed state, the exit detection system is adapted to issue an exit alert in response to the occupant of the person support apparatus moving toward exiting the person support apparatus. When in the disarmed state, the exit detection system is adapted to not issue the exit alert in response to an occupant of the person support apparatus moving toward exiting the person support apparatus. The exit detection system comprises a plurality of force sensors adapted to output signals corresponding to downward forces exerted on the litter frame. The controller is in communication with the plurality of force sensors, the exit detection system, and the obstruction sensor. The controller is further adapted to automatically switch the exit detection system from the armed state to the disarmed state in response to the obstruction sensor detecting contact with an obstruction.

According to other aspects of the present disclosure, the person support apparatus may be adapted to automatically send a notification to a remote server in response to detecting the contact with the obstruction, wherein the notification indicates that the controller has switched the exit detection system to the disarmed state.

In some embodiments, the controller is further adapted to automatically switch the exit detection system back to the armed state from the disarmed state in response to the obstruction sensor no longer detecting contact with the obstruction.

In some embodiments, the obstruction sensor is attached to an underside of the litter frame.

The exit detection system, in some embodiments, is adapted, when in the armed state, to calculate a center of gravity of the occupant, to compare the calculated center of gravity of the occupant to a boundary of a zone, and to issue the exit alert if the calculated center of gravity is outside of the boundary of the zone. In such embodiments, the controller may further be adapted change at least one of a size, shape, or location of the zone in response to movement of a component of the person support apparatus.

The person support apparatus, in some embodiments, may further comprise a second obstruction sensor, in which case the controller is adapted to automatically switch the exit detection system from the armed state to the disarmed state in response to either the first obstruction sensor or the second obstruction sensor detecting contact with an obstruction.

According to another embodiment of the present disclosure, a person support apparatus is provided that includes a litter frame, a lift system, a support deck, an obstruction sensor, an exit detection system, and a controller. The lift system is adapted to raise and lower a height of the litter frame. The support deck is supported on the litter frame and adapted to support thereon an occupant of the person support apparatus. The obstruction sensor is adapted to detect when the litter frame contacts an obstruction during movement of the litter frame. The exit detection system is adapted to be in an armed state and a disarmed state. When in the armed state, the exit detection system is adapted to issue an exit alert in response to the occupant of the person support apparatus moving toward exiting the person support apparatus. When in the disarmed state, the exit detection system is adapted to not issue the exit alert in response to an occupant of the person support apparatus moving toward exiting the person support apparatus. The exit detection system comprises a plurality of force sensors adapted to output signals corresponding to downward forces exerted on the litter frame. The controller is in communication with the plurality of force sensors, the exit detection system, and the obstruction sensor. The controller is further adapted to automatically issue the exit alert in response to the obstruction sensor detecting contact with an obstruction when the exit detection system is in the armed state.

According to other aspects of the present disclosure, the controller may further be adapted to not issue the exit alert in response to the obstruction sensor detecting contact with the obstruction when the exit detection system in is the disarmed state.

In some embodiments, the exit alert includes transmitting an exit alert message to a remote server.

In some embodiments, the controller is further adapted to automatically terminate the exit alert in response to the obstruction sensor no longer detecting contact with the obstruction.

The controller, in some embodiments, may further be adapted to issue an obstruction alert in response to the obstruction sensor detecting contact with the obstruction when the exit detection system is in the disarmed state.

In some embodiments, the person support apparatus further comprises a second obstruction sensor adapted to detect when the litter frame contacts an obstruction during movement of the litter frame. In such embodiments, the controller is adapted to automatically issue the exit alert in response to either the obstruction sensor or the second obstruction sensor detecting contact with the obstruction when the exit detection system is in the armed state.

According to still another embodiment of the present disclosure, a person support apparatus is provided that includes a litter frame, a lift system, a support deck, an obstruction sensor, an exit detection system, and a controller. The lift system is adapted to raise and lower a height of the litter frame. The support deck is supported on the litter frame and adapted to support thereon an occupant of the person support apparatus. The obstruction sensor is adapted to detect when the litter frame contacts an obstruction during movement of the litter frame. The exit detection system is adapted to be in an armed state and a disarmed state. When in the armed state, the exit detection system is adapted to issue an exit alert in response to the occupant of the person support apparatus moving toward exiting the person support apparatus. When in the disarmed state, the exit detection system is adapted to not issue the exit alert in response to an occupant of the person support apparatus moving toward exiting the person support apparatus. The exit detection system comprises a plurality of force sensors adapted to output signals corresponding to downward forces exerted on the litter frame. The controller is in communication with the plurality of force sensors, the exit detection system, and the obstruction sensor. The controller is further adapted to automatically change operation of the exit detection system in a first manner in response to the obstruction sensor detecting contact with an obstruction when the exit detection system is in the armed state.

According to other aspects of the present disclosure, the exit detection system may be adapted operate with a plurality of different sensitivity levels, and the controller may be adapted to change the operation of the exit detection system in the first manner by switching the exit detection system from a first sensitivity level to a second sensitivity level. In such embodiments, the second sensitivity level is less sensitive than the first sensitivity level such that, when operating with the second sensitivity level, the occupant needs to move closer to an edge of the person support apparatus to trigger the exit alert than the occupant needs to move to trigger the exit alert when operating with the first sensitivity level.

In some embodiments, the exit detection system is adapted, when in the armed state, to calculate a center of gravity of the occupant, to compare the calculated center of gravity of the occupant to a boundary of a zone, and to issue the exit alert if the calculated center of gravity its outside of the boundary of the zone, and the controller is further adapted to change the operation of the exit detection system in the first manner by changing at least one of a size, shape, or position of the zone.

In some embodiments, the controller is adapted to change the operation of the exit detection system in the first manner by adjusting the calculated center of gravity in a manner that compensates for changes in the signals of the force sensors that are due to contact with the obstruction.

In some embodiments, the person support apparatus includes at least first and second obstruction sensors that are adapted to detect when different portions of the litter frame contact the obstruction during movement of the litter frame. In such embodiments, the controller may be adapted to automatically change operation of the exit detection system in a second manner different from the first manner in response to the second obstruction sensor detecting contact with the obstruction when the exit detection system is in the armed state.

Before the various embodiments disclose herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
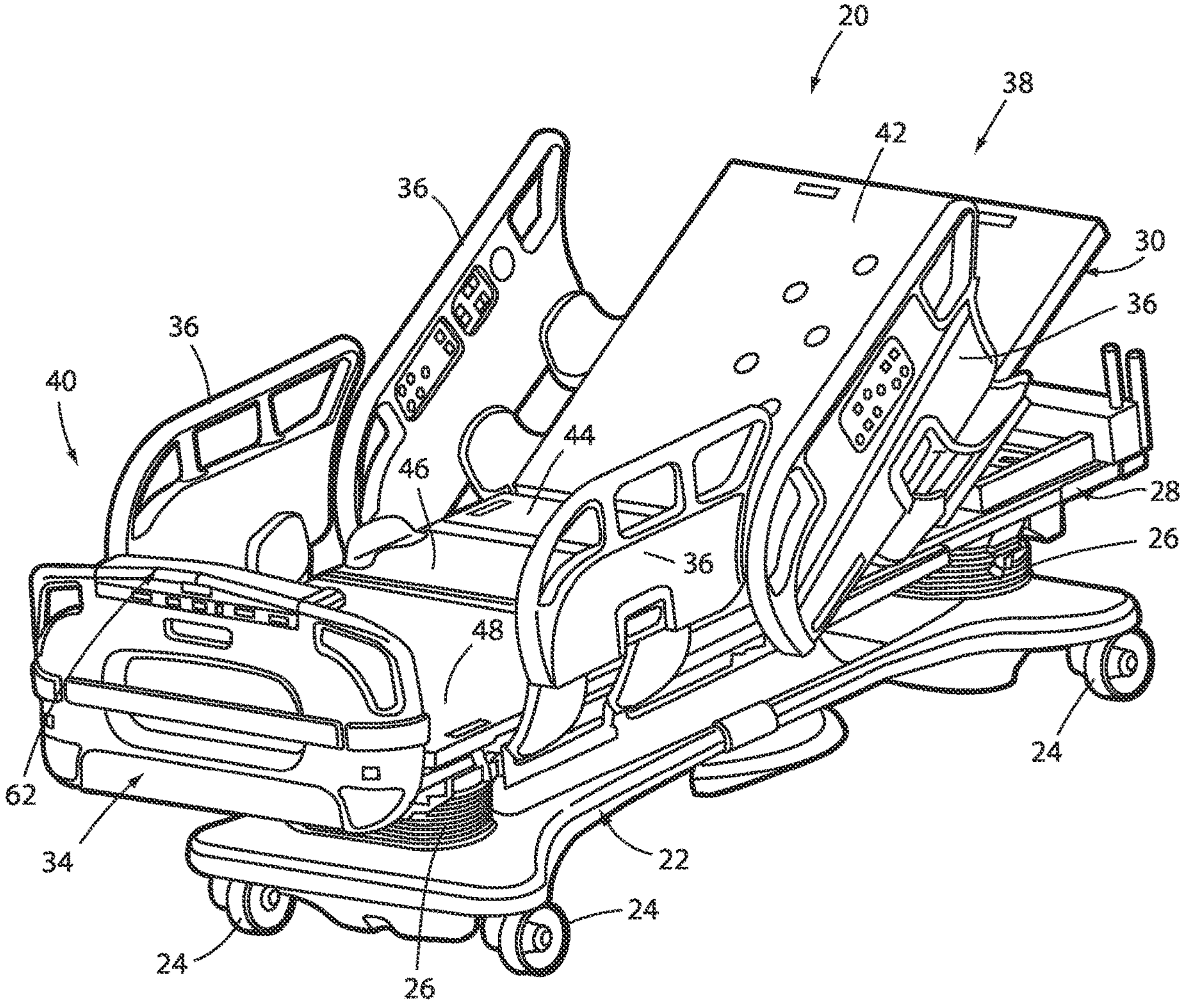
FIG. 1 is a perspective view of a person support apparatus into which one or more aspects of the present disclosure may be incorporated.

An illustrative person support apparatus 20 that may incorporate one or more aspects of the present disclosure is shown in FIG. 1. Although the particular form of person support apparatus 20 illustrated in FIG. 1 is a bed adapted for use in a hospital or other medical setting, it will be understood that person support apparatus 20 could, in different embodiments, be a cot, a stretcher, a gurney, a recliner, an operating table, or any other structure capable of supporting a person, whether stationary or mobile and/or whether medical or residential.

In general, person support apparatus 20 includes a base 22 having a plurality of wheels 24, a pair of lifts 26 supported on the base, a litter frame 28 supported on the lifts 26, and a support deck 30 supported on the litter frame 28. Person support apparatus 20 further includes a headboard (not shown), a footboard 34, and a plurality of siderails 36. Siderails 36 are all shown in a raised position in FIG. 1 but are each individually movable to a lower position in which ingress into, and egress out of, person support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment of FIGS. 1-3, lifts 26 are operable independently so that the tilting of litter frame 28 with respect to base 22 can also be adjusted. That is, litter frame 28 includes a head end 38 and a foot end 40, each of whose height can be independently adjusted by the nearest lift 26. Person support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard (not shown), footboard 34, and siderails 36. Support deck 30 provides a support surface for a mattress (not shown in FIG. 1), or other soft cushion, so that a person may lie and/or sit thereon. The top surface of the mattress or other cushion forms a support surface for the occupant. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Support deck 30 is, in the embodiment shown in FIG. 1, movable on litter frame 28 in a longitudinal direction. That is, support deck 30 is adapted to move on litter frame 28 toward and away from head end 38 and foot end 40. In one embodiment, person support apparatus 20 is mechanically constructed such that pivoting of head section 42 about its associated horizontal pivot axis occurs simultaneously with longitudinal movement of support deck 30 along litter frame 28. More specifically, in this embodiment, support deck 30 moves longitudinally along litter frame 28 toward foot end 40 when head section 42 pivots downwardly toward a flat orientation, and support deck 30 moves longitudinally along litter frame 28 toward head end 38 when head section 42 pivots upwardly toward a raised orientation.

Figure 2:
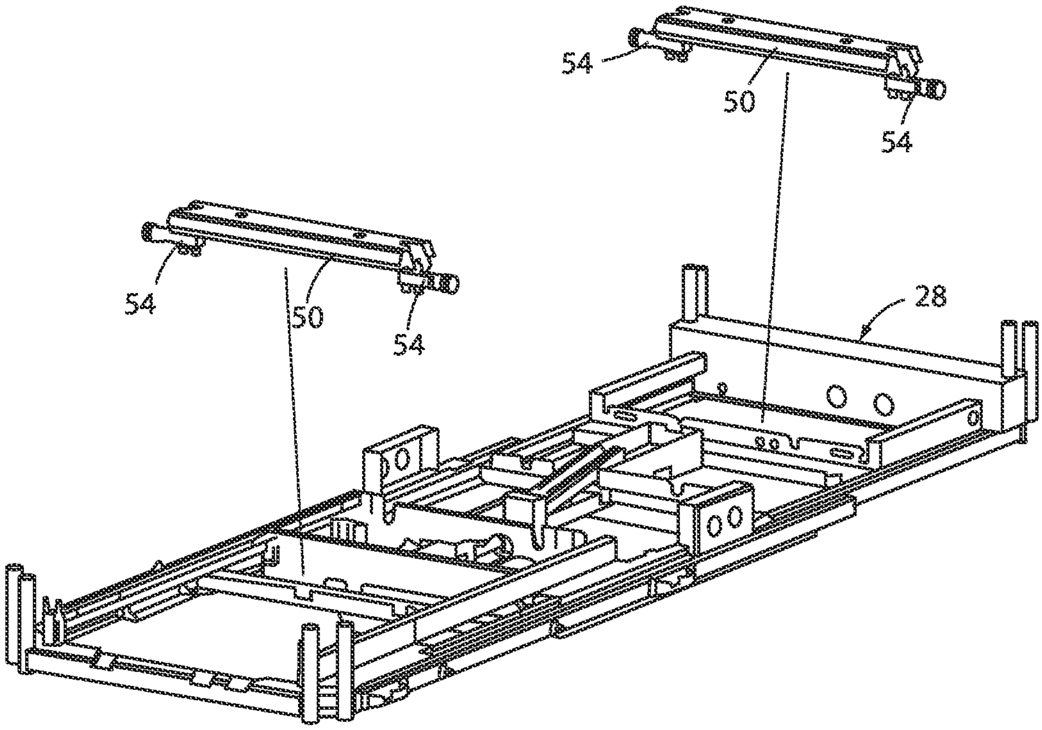
FIG. 2 is a perspective view of a litter frame of the person support apparatus of FIG. 1.

FIG. 2 illustrates in greater detail litter frame 28 separated from lifts 26 and base 22. Litter frame 28 is also shown in FIG. 2 with support deck 30 removed. Litter frame 28 is supported by two lift header assemblies 50. A first one of the lift header assemblies 50 is coupled to a top 52 (FIG. 3) of a first one of the lifts 26, and a second one of the lift header assemblies 50 is coupled to the top 52 of the second one of the lifts 26. Each lift header assembly 50 includes a pair of load cells 54. The illustrated embodiment of person support apparatus 20 therefore includes a total of four load cells 54, although it will be understood by those skilled in the art that different numbers of load cells may be used in accordance with the principles of the present disclosure. Load cells 54 are configured to support litter frame 28. More specifically, load cells 54 are configured such that they provide complete and exclusive mechanical support for litter frame 28 and all of the components that are supported on litter frame 28 (e.g. support deck 30, footboard 34, the headboard, siderails 36, etc.). Because of this construction, load cells 54 are adapted to detect the weight of not only those components of person support apparatus 20 that are supported by litter frame 28 (including litter frame 28 itself), but also any objects or persons who are wholly or partially being supported by support deck 30. The outputs of load cells 54 are fed into an exit detection system described in greater detail below.

In some alternative embodiments, person support apparatus 20 is constructed with load cells positioned in locations other than litter frame 28. For example, in at least one alternative embodiment, the person support apparatus is constructed with base frame load cells resting on a wheel frame having a construction of the type disclosed in commonly assigned U.S. patent application Ser. 16/917,004 filed Jun. 30, 2020, by Sukumaran et al and entitled PERSON SUPPORT APPARATUS WITH ADJUSTABLE EXIT DETECTION ZONES, the complete disclosure of which is herein incorporated by reference in its entirety. When a person support apparatus is constructed with the base and wheel frame construction of the type disclosed in this application, the load cells may be positioned on the wheel frame such that the entire weight of the base frame is supported on the load cells. Still other manners of positioning the load cells within the person support apparatus, and/or other locations for the load cells, may be utilized.

Further, as disclosed in the '004 application, person support apparatus 20 can include features for extending the width of its support deck 30 to accommodate patients of varying sizes. The width may be adjusted in any increments, for example between a first or minimum width, a second or intermediate width, and a third or expanded/maximum width. The exit detection system of the present disclosure may be configured to make automatic adjustments in response to the width adjustment features of the '004 application so that the width adjustments do not trigger a false occupant exit alert.

Figure 3:
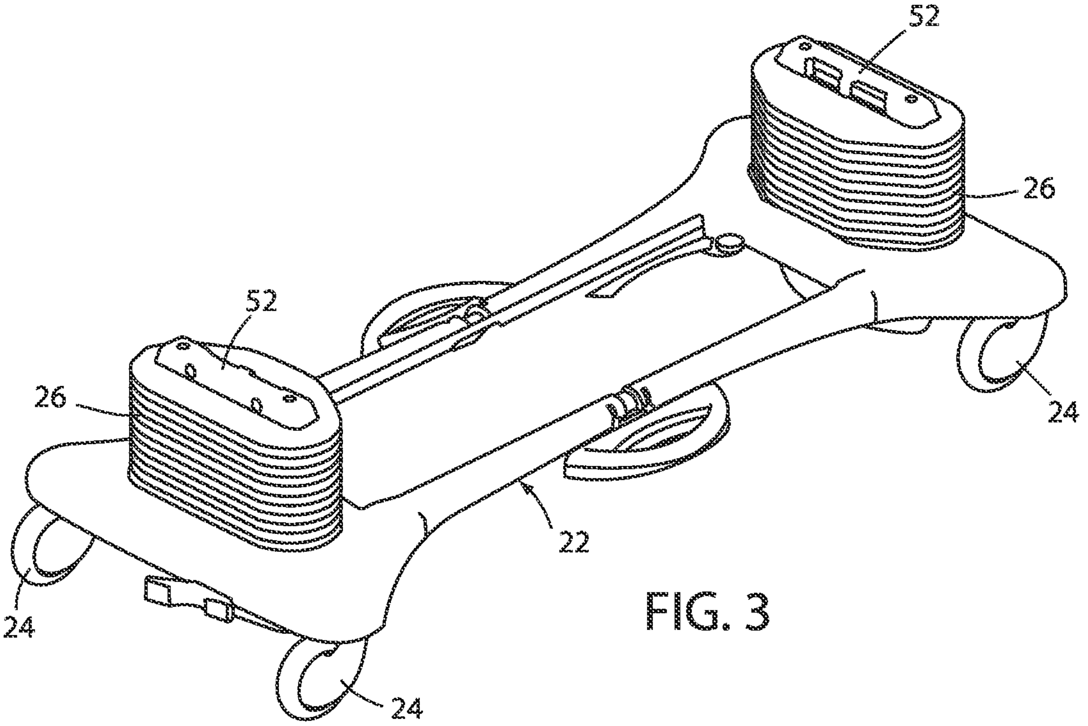
FIG. 3 is a perspective view of a base of the person support apparatus of FIG. 1.

As shown in FIGS. 1-3, the mechanical construction of person support apparatus 20 is similar to the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that person support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. No. 8,689,376 issued to Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of person support apparatus 20 may also take on forms different from what is disclosed in the aforementioned references.

Figure 4:
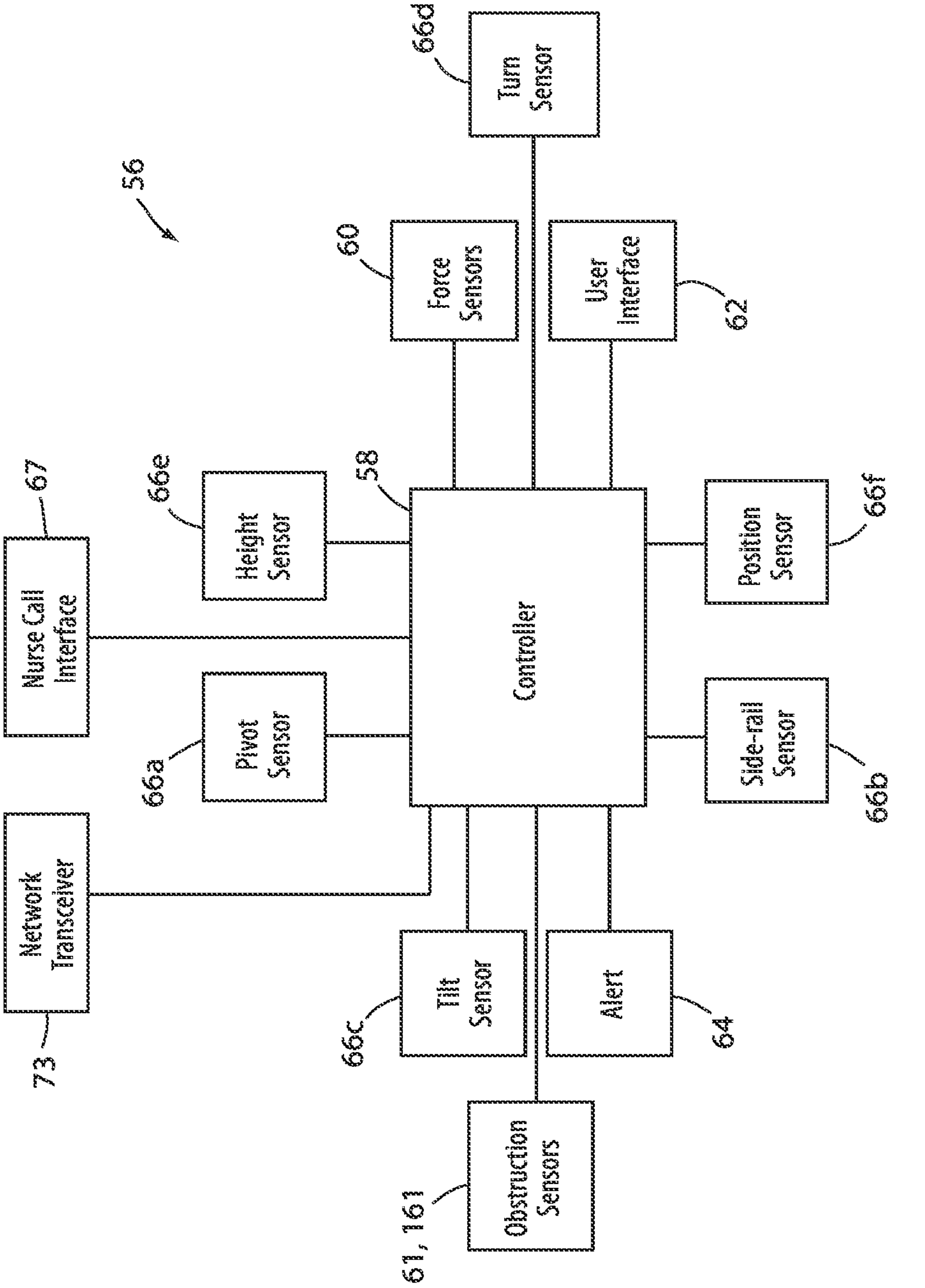
FIG. 4 is a block diagram of a control system that may be incorporated into the person support apparatus of FIG. 1.

As shown in FIG. 4, person support apparatus 20 includes a control system 43 that oversees the electromechanical operation of person support apparatus 20. Control system 43 includes an exit detection system 56, one or more obstruction sensors 61, 161, a plurality of other sensors 66*a-f*, a user interface 62, an alert 64, a nurse call interface 67, and a network transceiver 73. Control system 43 may also include additional components not illustrated in FIG. 4, such as, but not limited to, one or more motors for driving lifts 26 and/or for moving other components of person support apparatus 20. Control system 43 may also be modified to include fewer components than what is shown in FIG. 4. For example, in some modified embodiments, control system 43 does not include any of sensors 66*a-f*, and/or it includes one or more of sensors 66*a-f* but does not have exit detection system 56 utilize their outputs. Still other variations are possible.

Exit detection system 56 is adapted to determine when an occupant, such as, but not limited to, a patient, of person support apparatus 20 is likely to exit person support apparatus 20. More specifically, exit detection system 56 is adapted to determine when an occupant is likely to leave prior to the occupant actually leaving, and to issue an alert and/or notification to appropriate personnel so that proper steps can be taken in response to the occupant's imminent departure in a timely fashion. The particular structural details of exit detection system 56 can vary widely. It will be understood by those skilled in the art that components of exit detection system 56 may be added or omitted from one or more of the embodiments of exit detection system 56 that are discussed herein.

In the embodiment shown in FIG. 4, exit detection system 56 includes a controller 58 and a plurality of force sensors 60. Exit detection system 56 may be in communication with one or more obstruction sensors 61, 161, user interface 62, alert 64, and/or one or more of sensors 66*a-f*. Sensors 66*a-f* may take on any of a variety of different forms, including one or more load cells, pressure sensors such as piezoelectric and piezoresistive sensors, Hall Effect sensors, capacitive sensors, resonant sensors, thermal sensors, limit switches, gyroscopes, accelerometers, motion sensors, ultrasonic sensors, range sensors, potentiometers, magnetostrictive sensors, electrical current sensors, voltage detectors, and/or any other suitable types of sensors for carrying out their associated functions. Regardless of the specific form, the sensors 66*a-f* report outputs to controller 58 and controller 58 uses the output, in at least some embodiments, to adjust an alert zone of the exit detection system, to adjust an arming zone of the exit detection system 56, and/or to apply a compensation factor to either a calculated center of gravity of the occupant or to one or more ratios of the outputs of force sensors 60.

Force sensors 60 are adapted to detect downward forces exerted by an occupant of support deck 30. Thus, when an occupant is positioned on support deck 30 and substantially still (i.e. not moving in a manner involving accelerations that cause forces to be exerted against support deck 30), force sensors 60 will detect the weight of the occupant (as well as the weight of any components of person support apparatus 20 that are supported—directly or indirectly—by force sensors 60). In at least one embodiment, force sensors 60 are the same as, and positioned in the same locations as, load cells 54, as shown in FIG. 2. It will be understood by those skilled in the art, however, that force sensors 60 may be implemented as other types of sensors, such as, but not limited to, linear variable displacement transducers and/or any one or more capacitive, inductive, and/or resistive transducers that are configured to produce a changing output in response to changes in the force exerted against them.

Obstruction sensors 61, 161 are adapted to detect the presence of an obstruction (e.g., chair rail, shelf, window ledge, equipment, etc.) in contact with the person support apparatus. An obstruction can be anything that impedes or prevent passage or progress of the person support apparatus or a portion thereof. In a hospital environment, some typical obstructions that can be encountered include medical equipment, patient personal items, furniture, and fixtures. Obstructions are generically represented by reference numeral 57 throughout the drawings and it will be understood by a person of ordinary skill in the art that the shape, size, and other characteristics of obstructions can vary because an obstruction can be essentially any object foreign to the person support apparatus. It will also be understood that the terms "obstruction" and "obstacle" are used synonymously herein.

That is, an obstruction can be essentially any tangible thing that is fixed or moveable with respect to the person support apparatus that the person support apparatus (or portion thereof) becomes obstructed by through movement of the person support apparatus (or portion thereof), movement of the obstruction, or a combination of movement of the person support apparatus and the obstruction. When an obstruction is encountered by the person support apparatus, one or more of the obstruction sensors 61, 161 will detect the obstruction. Details of obstruction sensors 61 and 161 are provided below with respect to FIGS. 5-10. Still other types of obstruction sensors may be used with person support apparatus. Further, it will be understood that the number of obstruction sensors can be varied in different embodiments, ranging anywhere from a single obstruction sensor 61 or 161 (or another type) to four or more obstruction sensors.

Obstruction sensors 61, 161 can be installed at various locations about the person support apparatus, not just the locations illustrated and described in connection with FIGS. 5-10 to provide obstruction detection in different areas. Although switches are utilized in the embodiments of FIGS. 5-10, it will be understood by those skilled in the art that obstruction sensors 61 and/or 161 may be implemented as other types of sensors, such as, but not limited to, any one or more of capacitive, inductive, photoelectric, infrared, ultrasonic, resistive sensors that are configured to produce a changing output in response to changes in force due to the obstruction.

In some embodiments, some or all of the obstruction sensors can take the form of one or more actuator control systems. That is, in some embodiments, obstruction detection can be achieved or complemented by configuration of a controller to monitor current draw and/or overcurrent conditions of the lifts 26 or other actuator system(s) (e.g. Fowler, knee, and foot actuators) on the person support apparatus 20. By monitoring current draw of the lifts 26, the controller 58 can interpolate and detect obstruction conditions. For example, when raising the litter frame 28, if the litter frame encounters an obstruction the current draw for that respective actuator will begin to spike and eventually exceed normal current draw limits relative to load. Accordingly, the controller 58 can identify an obstruction has been encountered and can react accordingly, as discussed in more detail in connection with the control system. One person support apparatus implementing this form of obstruction detection is described in U.S. Pat. No. 10,206,834, filed Dec. 2, 2015, issued to Furman et al. and entitled OBSTRUCTION DETECTION SYSTEM AND METHOD, which is herein incorporated by reference in its entirety.

Pivot sensor 66*a*, in one embodiment, detects a pivot angle between head section 42 and a plane generally defined by litter frame 28. In some embodiments, pivot sensor 66*a* does not directly measure this pivot angle, but instead indirectly measures angle 70 by measuring the angle of another component of person support apparatus 20 whose angular orientation has a known relationship with this angle, or by measuring the position of another component of person support apparatus 20 whose position has a known relationship with this angle.

Each siderail sensor 66*b* is adapted to detect whether the siderail 36 it is associated with is in an up position or a down position. In some embodiments, siderails 36 are also movable to one or more intermediate positions. In those embodiments, siderails sensors 66*b* can be adapted to detect if their associated siderail 36 is in an intermediate position. In the embodiment of person support apparatus 20 shown in FIG. 1, there are four siderails 36 and thus four siderail sensors 66*b*, each of which senses the position of one of the four siderails 36.

Siderail sensors 66*b* can act as obstacle sensors in some embodiments. For example, in embodiments where the siderails are electrically actuated, the current draw and/or overcurrent associated with the actuator system for the siderails can be monitored and act as siderail sensors 66*b*. That is, an expected electrical signal output can be monitored for the various positions or for an expected transition between the up and down siderail position. Where current draw does not meet a predetermined baseline or other expectation, or an overcurrent or other pattern of current draw can complement or be deterministic of an obstruction detection. Further, even in non-electrical embodiments where the siderail sensors can sense movement between two or more positions, an obstruction may be sensed by transition from an up (or down) siderail state being initiated but the siderail never reaching the target state.

Alternatively, or in addition to siderail sensors 66*b*, each siderail 36 may include one or more obstruction sensors 61, 161. For example, one or more obstruction switches similar to the obstruction sensors described in connection with FIGS. 5-10 can be utilized in connection with the siderail. A switch plate for such configuration may or may not be installed along the bottom surface of the siderail to provide a larger surface area for an obstruction to engage and trigger the obstruction detection. In operation, if an obstruction switch is installed on the bottom surface of the siderail and an obstruction is encountered between the siderail 36 and the ground as the siderail is moved from the up to the down position, the obstruction switch is activated and signals that an obstruction has been encountered. The exit detection system (and/or other systems) can react to the obstruction detection, as discussed in more detail below.

Tilt sensor 66*c* detects a tilt angle 72 of litter frame 28 with respect to horizontal. In one embodiment, tilt sensor 66*c* measures this angle directly. In other embodiments, tilt sensor 66*c* comprises two sensors that detect the distance which each of lifts 26 are extended and circuitry that calculates the tilt angle of litter frame 28 with respect to horizontal from these two distances. In still other embodiments, tilt sensors 66*c* takes on other forms. One or more additional tilt angle sensors may also be included that measure a tilt angle of litter frame 28 that changes as a result of tilting about a longitudinal axis of person support apparatus 20 (i.e. a first side of litter frame 28 changes its height with respect to the second side).

The tilt sensor 66*c* can act as an obstacle sensor in some embodiments. In such embodiments, tilt sensor 66*c* can indicate an obstruction has been encountered by litter frame 28 if the reported angle from tilt sensor 66*c* differs from what would be expected for litter frame 28 (as determined, for example, by the commanded extensions of lifts 26). In other words, control system 43 can compute the expected tilt angle of litter frame 28 from the commands that it gives to lifts 26, compare that expected angle to the angle reported from tilt sensor 66*c*, and conclude that an obstruction has been detected if the expected angle differs from the reported angle by more than a threshold.

Turn sensor 66*d* detects a turn angle of a turning mechanism, such as a powered mattress having one or more inflatable turning bladders (not shown), that is used to turn an occupant of person support apparatus 20. Turn sensor 66*d* is, in at least one embodiment, positioned inside of the mattress (not shown) and measures turn angle directly. In other embodiments, turn sensor 66*d* measures one or more inflation pressures of one or more bladders inside of the mattress and estimates turn angle based upon the one or more measured inflation pressures.

Height sensor 66*e* detects either an absolute or relative height of litter frame 28. More specifically, in one embodiment, height sensor 66*e* detects how far each lift 26 has extended from its lowest position. In another embodiment, height sensor 66*e* detects how high one or more points on litter frame 28 (or any component of person support apparatus 20 non-movably coupled to litter frame 28) is with respect to a reference (e.g. a floor, base 22, etc.).

Position sensor 66*f* detects the longitudinal position of support deck 30 relative to litter frame 28. That is, as noted previously, support deck 30 is longitudinally movable, in some embodiments, with respect to litter frame 28. In some embodiments, person support apparatus 20 is constructed such that the longitudinal position of support deck 30 relative to litter frame 28 is directly correlated to a pivot angle of the head section 42. In such embodiments, position sensor 66*f* and pivot angle sensor 66*a* may be one and the same. In still other embodiments, person support apparatus 20 may be constructed such that the longitudinal position of support deck 30 relative to litter frame 28 is directly correlated to the position and/or orientation of some other component of person support apparatus, in which case position sensor 66*f* may be configured to measure the position of support deck 30 indirectly by measuring the position or orientation of the other component. In other embodiments, support deck 30 may be positioned at a longitudinally and laterally fixed location with respect to litter frame 28, and position sensor 66*f* may be omitted.

All of the sensors 66 are in communication with controller 58 (FIG. 4). Controller 58 is constructed of any electrical component, or group of electrical components, that are capable of carrying out the functions described herein. In many embodiments, controller 58 is a conventional microcontroller, although not all embodiments need include a microcontroller. In general, controller 58 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 58 in carrying out the functions described herein, as well as the data for carrying out these functions, are stored in a memory (not labeled) accessible to controller 58.

Controller 58 is also in communication with user interface 62. User interface 62 is implemented in the embodiment shown in FIG. 1 as a control panel having a lid (flipped down in FIG. 1) underneath which is positioned a plurality of controls. The controls—which may be buttons, dials, switches, or other devices—allows a user to control various aspects of exit detection system 56. User interface 62 may also include a display for displaying information regarding exit detection system 56 and other aspects of person support apparatus 20. Although FIG. 1 illustrates user interface 62 mounted to footboard 34, it will be understood that user interface 62 can be positioned elsewhere, and/or that one or more additional user interfaces can be added to person support apparatus 20 in different locations, such as the siderails 36, for controlling various aspects of exit detection system 56 or other systems of the person support apparatus.

In one embodiment, user interface 62 includes a control that enables a user to arm and disarm exit detection system 56, as well as allowing a user to select different sensitivity levels which are used for triggering an exit alert, as will be discussed in greater detail below. In at least some embodiments, the controls also allow a user to configure the alerting features of exit detection system 56, including choosing from amongst the different types of alerts that can be issued by exit detection system 56. Such types include local alerts (issued at person support apparatus 20), remote alerts (issued at a remote location, such as a nurse's station, hallway light, or to mobile communication devices carried by personnel), audio alerts, visual alerts, and/or any combinations of these. The user interface can also include a variety of options with regard to configuration of the obstruction detection features including both the associated alerting features as well as other reactions to the detection of an obstruction, such as how other systems react to obstruction detection. In some embodiments, the exit detection system 56 is configurable to react to obstruction detection in a variety of different ways. The reactions can be configured for all obstruction detection or based on a region, area, or particular sensor or set of obstruction sensors.

In some embodiments, controller 58 of exit detection system 56 is adapted to determine the center of gravity of whatever load is applied to force sensors 60, compare that center of gravity to a zone, and issue an exit alert if the center of gravity moves outside of that zone. In other words, exit detection system 56 determines the center of gravity of the combined weight of an occupant, mattress, and/or any objects that are positioned on support deck 30 or litter frame 28, as well as those components of person support apparatus 20 whose weight is supported by force sensors 60 (e.g. litter frame 28, support deck 30, siderails 36, etc.) and compares it to an area of acceptable locations (i.e. a zone). If the center of gravity is not within than zone, this is indicative of the patient exiting, and an exit alert is issued. In one embodiment, exit detection system 56 determines this center of gravity using the system and method disclosed in commonly assigned U.S. Pat. No. 5,276,432 issued to Travis entitled PATIENT EXIT DETECTION MECHANISM FOR HOSPITAL BED, the complete disclosure of which is incorporated herein by reference in its entirety. In other embodiments, other algorithms may be used.

In some embodiments, exit detection system 56 is configured to distinguish between detected changes in the center of gravity of the load that are due to the occupant moving with respect to the support surface and changes in the detected center of gravity of the load that are due to movement of one or more components of the person support apparatus. Such movement includes, but is not limited to, pivoting of one or more sections of deck 30; tilting of litter frame 28; longitudinal movement of support deck 30 relative to litter frame 28; movement of one or more siderails 36 from an up position to a down positions, or vice versa; changes in height of litter frame 28; and/or therapeutic turning of the occupant by a turning device built into the mattress or otherwise positioned on top of support deck 30. Stated alternatively, in such embodiments, exit detection system 56 is configured to determine how much, if any, of the changes in the outputs of force sensors 60 is due to patient movement relative to support surface 31 and how much, if any, of the changes in the outputs of force sensors 60 is due to components of person support apparatus having moved. Exit detection system 56 may then compensate the readings it obtains from force sensors 60 in order to account for the changes that are due to components of person support apparatus 20 having moved. Manners in which this compensation may be applied are disclosed in U.S. patent publication 2020/0214599 to Kostic entitled EXIT DETECTION SYSTEM WITH COMPENSATION, the complete disclosure of which is incorporated herein by reference in its entirety.

Exit detection system 56, in at least one embodiment, is configured to distinguish between detected changes in the center of gravity of the load that are due to the occupant moving with respect to the support deck 30 and changes in the detected center of gravity of the load that are due to obstructions encountered by the person support apparatus. If an obstruction exerts a force on litter frame 28 or portion thereof (or any components, or portions thereof, supported by the litter frame) it will change the detected center of gravity of the load because that force, or a component of that force, will be detected by the load cells and will introduce an error into the calculation of the patient's center of gravity. As will be discussed in greater detail below, this error may be addressed in different manners, such as, but not necessarily limited to, removing this error from the center of gravity calculations and/or changing a size, shape, and/or location of an exit detection alert zone in a manner that addresses this error.

The changes in the center of gravity that are detected by exit detection system 56 as a result of an obstruction being impacted can vary. Generally speaking, exit detection system 56 is configured to detect changes in the center of gravity due to pivoting of one or more sections of deck 30 into an obstruction; tilting of litter frame 28 into an obstruction; longitudinal movement of support deck 30 relative to litter frame 28 such that an obstruction encounters the litter frame 28 or a component thereof; movement of one or more siderails 36 from an up position to a down positions such that an obstruction exerts an upward or downward force component on one or more of the siderails (or vice versa); and/or changes in height of litter frame 28 that cause the litter frame to experience an upward or downward force component from an obstacle. The exit detection system can also be configured to detect changes in the center of gravity due to movement of one or more obstructions with respect to the person support apparatus or a component thereof (i.e. an obstruction is moved into contact with person support apparatus 20, rather than person support apparatus moves into contact with an obstruction).

Control system 43 also includes a nurse call interface 67 and a network transceiver 73. Nurse call interface 67 is adapted to communicatively couple to a conventional nurse call system so that controller 58 is able to communicate information to the nurse call system, such as, but not limited to, an exit alert. In many instances, nurse call interface 67 is adapted to communicate information to the nurse call system by opening or closing one or more relays that are electrically coupled to pins of a 37-pin wall outlet positioned on the headwall of a typical hospital room. Further details about different embodiments of nurse call interface 67 are provided below.

Network transceiver 73 may be a wireless transceiver adapted to communicate with one or more wireless access points of the healthcare facility's local area network. In some embodiments, transceiver 73 may be a WiFi transceiver adapted to transmit and receive wireless electrical signals using any of the various WiFi protocols (IEEE 802.11, 801.11g, 802.11n, 802.11ac . . . , etc.). In other embodiments, network transceiver 73 may be a transceiver adapted to communicate using any of the frequencies, protocols, and/or standards disclosed in commonly assigned U.S. patent application Ser. No. 62/430,500 filed Dec. 6, 2016, by inventor Michael Hayes and entitled NETWORK COMMUNICATION FOR PATIENT SUPPORT APPARATUSES, the complete disclosure of which is incorporated herein by reference. In still other embodiments, transceiver 73 may be a wired transceiver that communicates with the healthcare facility local network over a wired connection, such as an Ethernet cable or the like. Regardless of whether transceiver 73 is a wired or wireless transceiver, it enables controller 58 to communicate with one or more servers on the healthcare facility's computer network.

Figure 5:
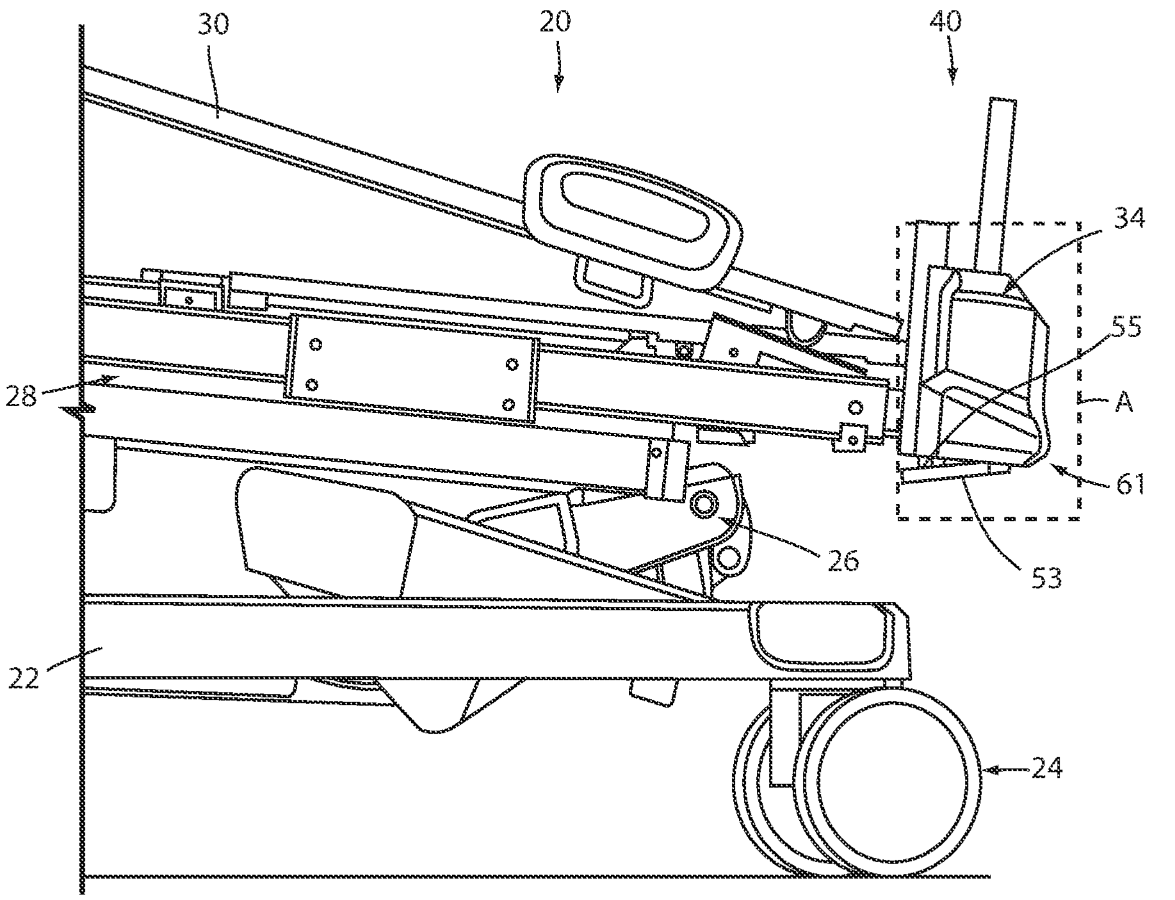
FIG. 5 is a side view of one embodiment of an obstruction detection sensor that may be incorporated into the person support apparatus of FIG. 1.
Figure 6:
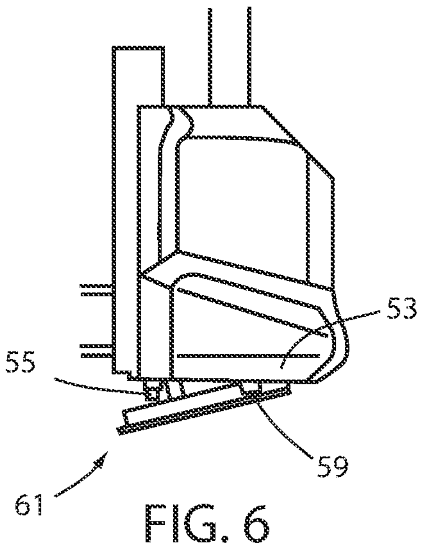
FIG. 6 is an enlargement of the area labeled A in FIG. 5 showing the obstruction detection sensor in a first state in which no obstruction is detected.
Figure 7:
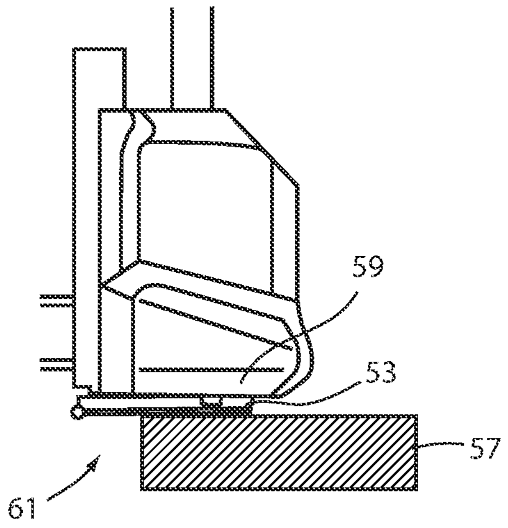
FIG. 7 is an enlargement of the area labeled A in FIG. 5 showing the obstruction detection sensor in a second state in which an obstruction has been detected.

FIGS. 5-7 illustrate a first type of obstruction detection sensor 61 that may be incorporated into person support apparatus 20. In this embodiment, obstruction sensor 61 includes a plunger style obstruction switch 55 and a switch plate 53 configured to cooperate to detect and transmit one or more obstruction detection signals in response to encountering an obstruction. Obstruction detection sensor 61 is installed near the foot end 40 of the person support apparatus 20 on the litter frame 28 or footboard 34. Although the obstruction sensor 61 of FIGS. 5-7 includes a single obstruction switch 55, it will be understood by those skilled in the art that different numbers and different types of obstruction sensors, related components, and combinations thereof, may be used in accordance with the principles of the present disclosure. For example, in alternative embodiments the obstruction sensor 61 can be implemented with one or more lever style switches. Further, capacitive, inductive, photoelectric, ultrasonic, resistive, or other types of sensors that are configured to produce a changing output in response to changes in force due to the obstruction can be utilized as an obstruction sensor in place of the obstruction switch 55 with or without a switch plate 53 or other sensor enhancing component.

Switch 55 is installed toward the bottom of the footboard 34 such that the plunger of the switch juts through an aperture in the litter frame 28 past the plane of the bottom of the footboard 34. FIG. 6 illustrates the switch 55 and switch plate 53 in their inactivated state where no obstruction is present. FIG. 7 illustrates the activated state where an obstruction 57 has physically displaced the switch plate 53 causing the plunger of switch 55 (not visible in FIG. 7) to depress. The switch plate 53 is pivotable about a generally horizontal pivot axis between a resting acute angle below the footboard 34 bottom plane (FIG. 6) and a range of raised positions toward the footboard 34 bottom plane (one of which is shown in FIG. 7). The pivot axis can be provided by a hinge 59 or other flexible joint installed toward the foot end of the bed, such as to the bottom of the footboard 34 or litter frame 28. The switch plate 53 extends downwardly from the underside of the litter frame 28 at an angle when it is not encountering an obstacle (FIG. 6). That is, the hinge 59 is configured such that in its normal, resting state where no obstruction is present the switch plate 53 extends at an angle from the bottom plane of the footboard 34 that clears the plungers of the switch 55. The switch plate is positioned on the underside of the litter frame 28 such that it will not come into contact with the base 22 of the person support apparatus 20. Specifically, the switch plate 53 is positioned outside of the footprint of the base 22 of the person support apparatus ensuring it will not be triggered (forced upwards) by contact with the base 22. This is true regardless of whether the litter frame is in longitudinally extended or retracted positions, and regardless of whether the litter frame 28 is in a Trendelenburg position, reverse Trendelenburg, or other available configuration. In alternative embodiments, the switch plate 53 may be positioned inside the footprint of the base 22 with a physical construction that ensures the person support apparatus 20 or component thereof cannot contact the outwardly facing surface of the switch plate 53 (i.e. the surface shown engaged with obstruction 57 in FIG. 7) through normal operation. In addition, or alternatively, the moveable aspects of the person support apparatus may be restricted by the controller to ensure the person support apparatus 20 or component thereof cannot contact the switch plate 53 through normal operation.

When an obstruction 57 forces the switch plate 53 upward, the switch plate pivots to a substantially flat orientation (FIG. 7) relative to the litter frame 28. That is, when an obstruction 57 is encountered by the person support apparatus 20 (e.g. by movement of the person support apparatus, movement of the obstruction, or both) the switch plate 53 is physically displaced by the obstacle causing the plate to pivot toward the bottom of the footboard 34 where the switch 55 is mounted. After sufficient force is applied by the switch plate 53 to physically depress the plunger of the switch 55, the switch activates and transmits one or more electrical signals indicative of detecting an obstruction. The signals are transmitted to a controller 58 located on the person support apparatus 20 for processing. Thus, if the litter frame 28 is being lowered and the switch plate 53 comes into contact with an obstacle, the switch plate 53 will, after sufficient force is applied, compress the switch, thereby causing the switch 55 to send a signal to controller 58.

Because of the construction illustrated in FIGS. 5-7 and described herein, obstruction switch 55 is adapted to detect the presence of any obstruction that causes the switch 55 to be physically displaced by a threshold amount sufficient to trigger or activate the switch. Accordingly, absence of an obstruction can also be detected by lack of physical displacement beyond a threshold or lack of any physical displacement. In the current embodiment, the output of the obstruction switch 55 is fed to a controller, such as the controller of the exit detection system described in greater detail below. The output of the obstruction switch 55 can also be fed to other systems instead of or in addition to the exit detection system. Some embodiments may include a motion interrupt system that prevents movement of the person support apparatus or a component thereof, such as the litter frame, in response to an obstruction detection signal. For example, a motion interrupt system, when triggered by detection of an obstacle or other object, can prevent the litter frame 28 from being further lowered or otherwise manipulated in such a way as to exacerbate an encounter between an obstacle and the person support apparatus.

In the current embodiment, the switch 55 provides a single output signal indicative of whether an obstruction is present or absent. The switch is configured to activate in response to force at or above a predetermined force threshold being applied to the plunger, which causes the switch to generate a single output. Accordingly, a single output signal can be provided that is indicative of whether an obstruction is present without having to compare multiple sensor signals. In alternative embodiments, the switch 55 can provide one or more output signals, including non-binary output signals such as values indicative of various characteristics of the switch (e.g. the obstruction detection signal being indicative of an amount of travel of the plunger, a plunger position, an operating force, a total travel force, an amount of displacement or other characteristic). It will be well understood by those of skill in the art, the dimensions and other mechanical characteristics along with operating characteristics of the switch 55 can vary along with its circuitry depending on the application. In the current embodiment, the switch 55 is a plunger style miniature door switch with a 9 mm long stroke. The switch can be implemented in a double throw, normally closed, normally open, or other configuration.

The illustrated embodiment of FIGS. 5-7 only has a single obstruction sensor in the form of switch 55 and switch plate 53. This enables obstruction detection in proximity to the lower portion of the foot end 40 of the bed. In some embodiments, an obstruction sensor can be located elsewhere on the person support apparatus 20 or additional obstruction sensors can be mounted elsewhere on the person support apparatus to provide additional obstruction detection signals that are indicative of obstruction encounters at other locations of the person support apparatus. Multiple obstruction sensors can also be mounted in relative proximity to provide increased obstruction detection accuracy, sensitivity, or to provide additional information regarding obstructions encountered in a particular area of the person support apparatus or characteristics of the encounter between the person support apparatus 20 and obstacle.

Figure 8:
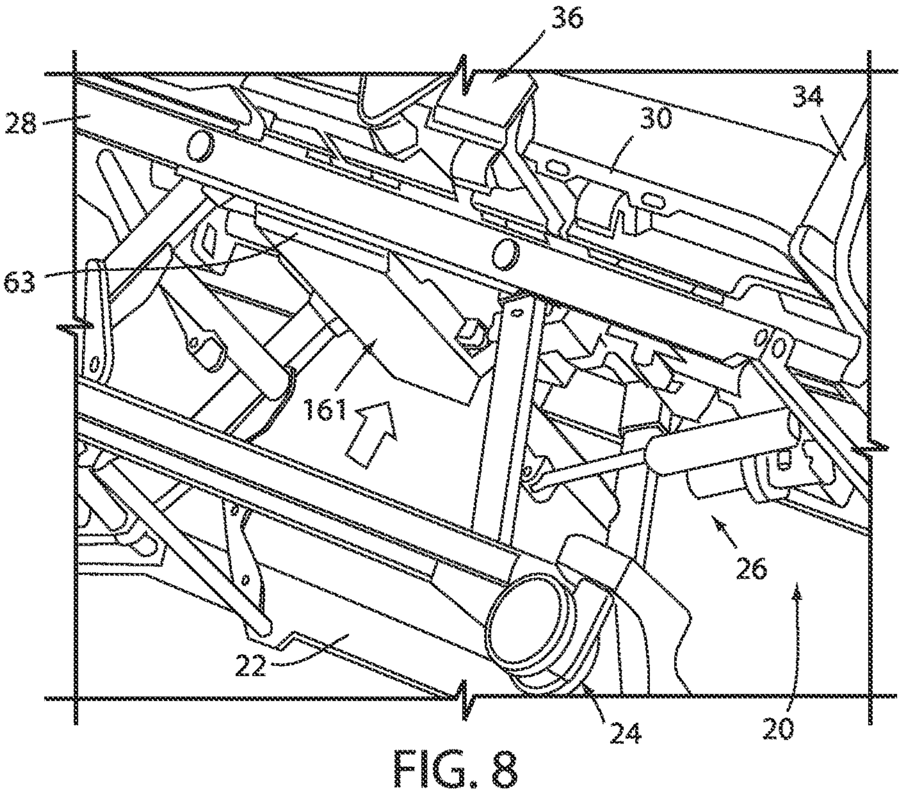
FIG. 8 is a partial perspective view of another obstruction detection sensor that may be incorporated into the person support apparatus of FIG. 1, either in addition to or in lieu of the obstruction detection sensor of FIGS. 5-7.
Figure 9:
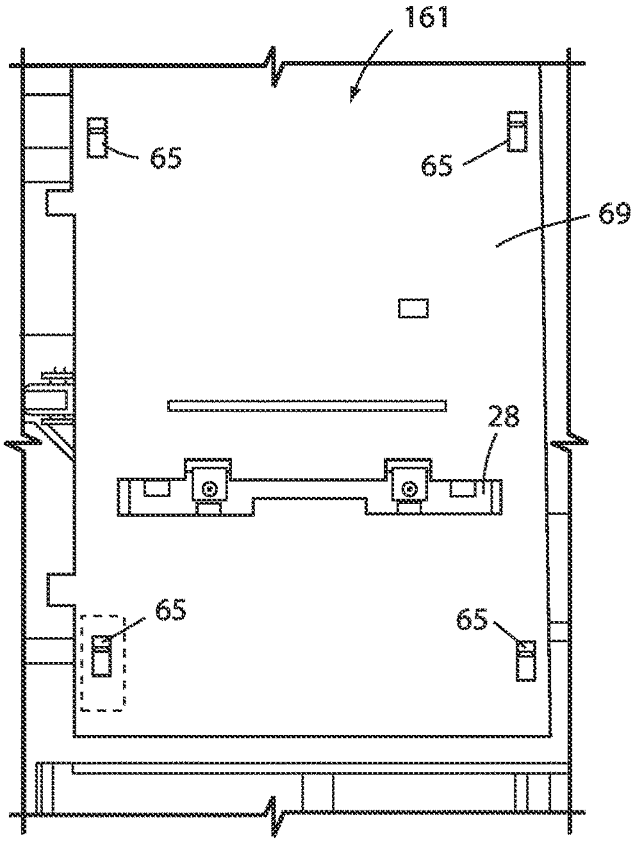
FIG. 9 is a bottom view of the obstruction detection sensor of FIG. 8 showing a belly pan of the obstruction detection sensor removed from the person support apparatus.
Figure 10:
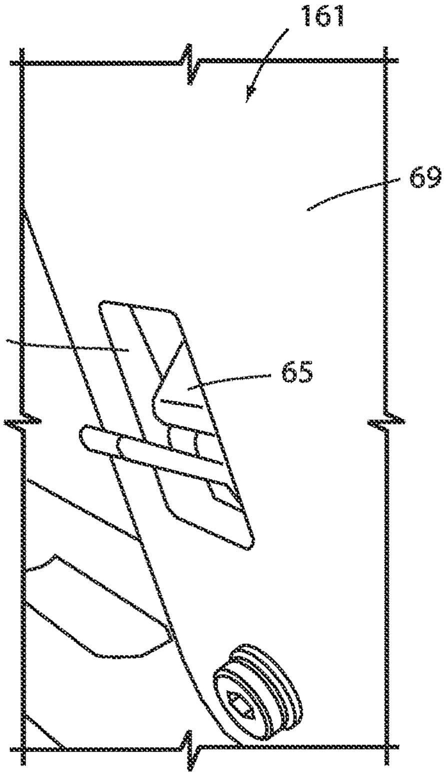
FIG. 10 is a close-up perspective view of one of the obstruction switches of the obstruction detection sensor of FIGS. 8 and 9.

One example of an alternative obstruction detector 161 is shown in more detail in FIGS. 8-10. Obstruction detector 161 differs from obstruction detector 61 primarily in the location at which it is attached to person support apparatus 20. As shown in FIG. 8, obstruction detector 161 is positioned generally in a center area of the underside of litter frame 28. Obstruction detector 161 includes four lever style obstruction switches 65 and a belly pan 63 (FIGS. 8-10). The switches 65 and belly pan 63 are configured to cooperatively detect and transmit one or more obstruction detection signals in response to encountering an obstruction. Although the obstruction detection sensor 161 of FIGS. 8-10 includes four obstruction switches 65, it will be understood by those skilled in the art that different numbers and different types of obstruction sensors, related components, and combinations thereof, may be used in accordance with the principles of the present disclosure.

FIG. 9 illustrates a bottom view of a mounting plate 69 joined to the litter frame 28 with all four switches 65 installed and the belly pan 63 removed. In the illustrated embodiment, the switches 65 are installed in four apertures 71 at the corners of mounting plate 69 such that the lever of each switch 65 juts through a corresponding aperture 71 past the plane of the bottom of the mounting plate 69.

FIG. 10 shows a close-up of one of the corner areas of the plate 69 showing the switch 65 lever extending and protruding through an opening 71 in the plate 69. The mounting plate 69 can be one piece or multiple sections. In the embodiment illustrated in FIGS. 8-10, the mounting plate 69 is two hinged electrical plate covers mounted at the middle section of the bed that span between two perimeter longitudinal rails of the litter frame 28.

A vacuum formed floating belly pan or cover 63 acts as an actuating barrier for the obstructions and subsequent activation of the underlying obstruction switches 65. The four switches 65 mounted near the outermost corner locations of the mounting plate 69 are covered by the belly pan 63 which also covers the hinged electrical plates 69 under the litter frame 28, perhaps as best shown in FIG. 8.

The floating cover 63, shown in FIG. 8, when mounted and constrained to the underside of the litter frame as shown, is permitted to float and is movable in the Z-direction (up/down) when installed relative to the litter frame 28 plate 69. As a result, the belly pan 63 acts against and activates any one or a combination of the four lever switches 65 when it is forced upward by an encountered obstruction. For example, an obstruction may be positioned underneath the litter frame 28 within the footprint of the base such that the belly pan 63 will meet or otherwise encounter the obstacle as the litter frame 28 is lowered. The encounter between the pan 63 and obstruction (not shown) will force the pan 63 upwards compressing one or more of the four switches 65, thereby causing one or more of the switches to send a signal to a microcontroller, such as controller 58 on board the person support apparatus 20. A control system can be configured with logic to utilize the obstruction signals, as will be discussed in greater detail below. Suffice it to say the control system can be configured to react to the obstruction detection, such as by changing the functionality of or adjusting one or more characteristics of the bed exit detection system.

Depending on the size and position of the obstruction, some, but not all of the obstruction switches 65 may or may not be activated contemporaneously. That is, the obstacle may be encountered toward one of the corners such that only one lever switch is thrown when the belly pan 63 is forced upwards. This is due to the floating configuration of the belly pan. The controller can be configured to infer obstruction position and/or other information about the obstruction based on which switches activate. That is, the controller can be configured to associate the obstruction switch 65 outputs with physical areas of the person support apparatus. Thus, information about where an obstacle is encountered can be inferred by which switches are activated and which are not. For example, if a single obstruction switch is triggered without any other switches being triggered, the position of the obstruction can be inferred to be the area associated with the position of the switch that triggered. Or, if two or more obstruction switches are triggered the position of the obstruction can be inferred to be the collective areas associated with the positions of the triggered switches. This information can be utilized to alert staff regarding the obstacle encounter. The information can also be utilized for performing targeted maintenance and repair on the person support apparatus.

Further, the controller can be configured to infer movement information about the encounter based on activation timing (e.g. timestamps) of the obstruction switches. That is, the order in which the switches activate is generally indicative of the movement associated with the encounter. When the activation timing of the obstruction switches is combined with movement data of the person support apparatus (e.g. actuation of the lift system), the controller can be configured to determine additional information about the cause of the obstruction encounter, which can be logged and/or otherwise provided to an operator of the person support apparatus or other personnel.

Exit detection system 56 is configured to cooperate with the obstruction detection sensors 61 and/or 161. That is, exit detection system 56 is configured to utilize the outputs from one or more obstruction detectors 61, 161 and change its operation in one or more manners in response to an obstruction being detected, and in some cases, in response to the obstruction no longer being detected. In some embodiments, exit detection system 56 is configured to react to the detection of an obstruction in one of three different manners: (1) by automatically disarming (if previously armed) the exit detection system in response to an obstruction being detected; (2) by automatically triggering an exit alert in response to an obstruction being detected; or (3) by automatically adjusting the calculations used for determining whether to issue an exit alert, wherein the adjustment attempts to account for, and thus remove, the changes in the outputs of the load cells that are due to the contact with the obstruction and that otherwise create errors in the calculated patient's center of gravity. Each of these three different manners of reacting are described in more detail with respect to algorithms 1200, 1300, and 1400 of FIGS. 11, 12, and 13, respectively.

Figure 11:
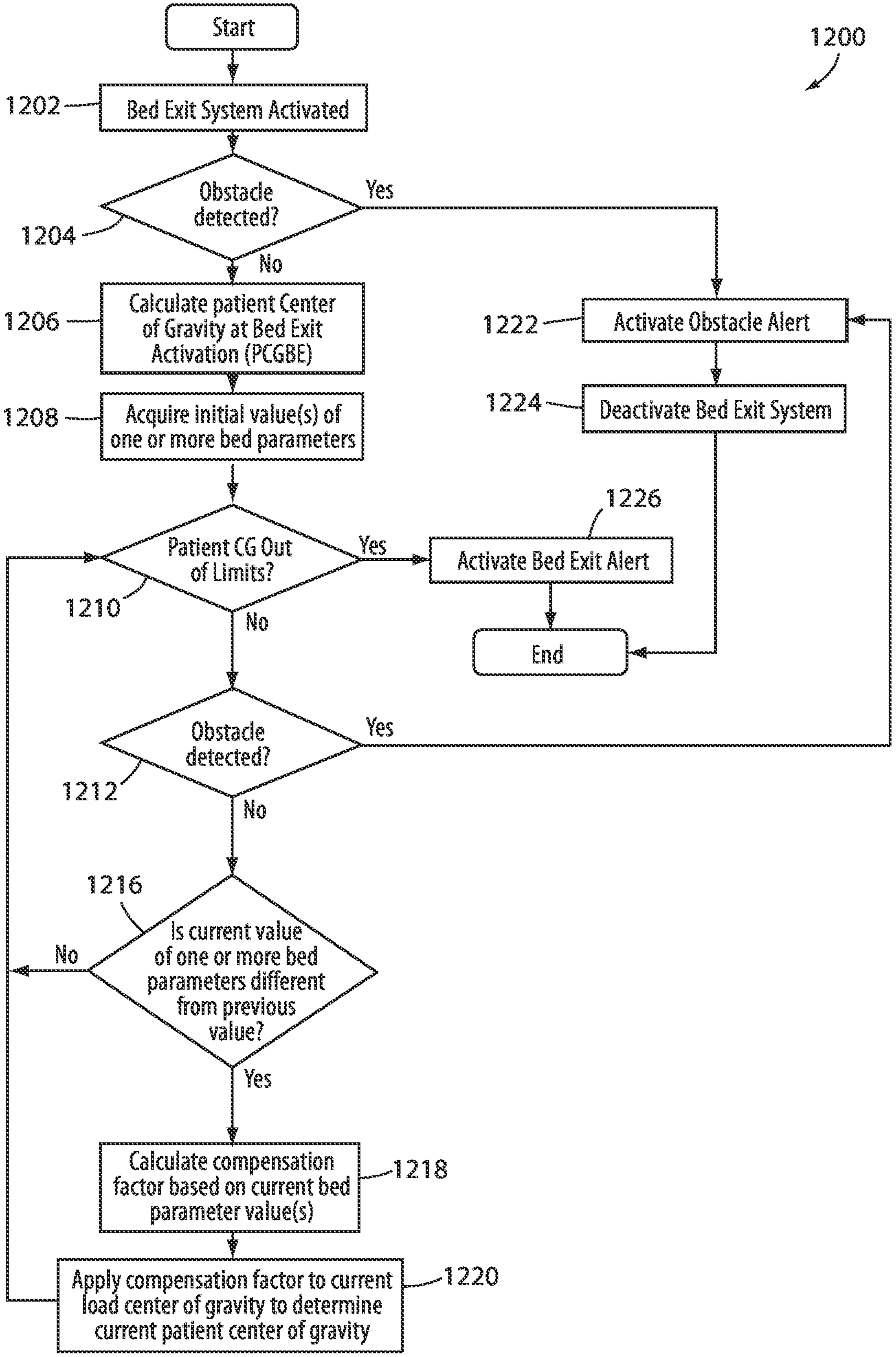
FIG. 11 is a flowchart of one embodiment of an exit detection algorithm that can be carried out by the exit detection system of the person support apparatus.

In the embodiment shown in FIG. 11, controller 58 is configured to execute algorithm 1200. In this particular embodiment, exit detection system 56 is configured to automatically disarm itself in response to the obstruction sensor 61 and/or 161 detecting contact with an obstruction. Exit detection algorithm 1200 begins at an initial step 1202 when exit detection system 56 is armed, such as by a user manipulating one or more controls on user interface 62. After being armed at step 1202, controller 58 proceeds to step 1204 where the controller 58 is configured to determine whether an obstruction is currently being encountered. This can be done by review of the obstruction sensor data or requesting a current sensor reading from one or more obstruction sensors. If an obstruction is present, the bed exit detection system 56 is configured to activate an obstruction alert at step 1222. The obstruction alert may be issued locally (by lights, sounds, and/or the display of selective content on a display onboard person support apparatus 20) and/or it may be issued remotely, such as by sending a notification message to a remote server and/or other recipient. In addition, in this embodiment, the bed exit system is automatically disarmed at step 1224, which ensures that no false positive bed exit system notifications are issued due to the inaccuracies introduced to the force sensors where an obstacle either adds or subtracts weight to or from the load cells 54.

If no obstruction is present, the system proceeds to calculate an initial center of gravity of the occupant of person support apparatus 20. This calculation is performed using known mathematical techniques for computing a center of gravity, as well as knowledge of the relative positions of the force sensors 60. Although other coordinate systems may be used, controller 58 computes the center of gravity using a planar coordinate system 86 (FIGS. 14C, 15C) having an x-axis 88 that is generally parallel to the foot end 40 of support deck 30 and a y-axis 90 that is generally parallel to a side of support deck 30. Other coordinate systems can be used. Regardless of which coordinate system is used, controller 58 knows the location of force sensors 60 in the particular coordinate system that is used. In the example shown in FIG. 14C, force sensors 60 are shown in known locations 87.

After determining the occupant's center of gravity at step 1206, controller 58 proceeds to step 1208 where it determines the initial value of one or more parameters of person support apparatus 20. More specifically, in the embodiment illustrated in FIG. 11, controller 58 determines the following values at step 1208: a current value of pivot angle 70; a current value of tilt angle 72, a current value of turn angle 74, a current value corresponding to the current relative longitudinal position of support deck 30 on litter frame 28, a current value of height 78, and a current value indicating the current position of each siderail 36 (up, down, or intermediate). It will be understood by those skilled in the art that, in other embodiments, algorithm 1200 can be modified to determine less than or more than these values. Indeed, in other embodiments, controller 58 can determine any one or more of these values at step 1208, or still other values.

After completing step 1208, controller 58 moves onto step 1210 (FIG. 11) where it determines whether the center of gravity of the occupant determined at step 1206 is outside of a predefined zone. The predefined zone, in one embodiment, is defined in coordinate system 86 and is a trigger controller 58 uses to determine whether or not to issue an exit alert, in at least one embodiment. Although other types of zones may be used, in the illustrated embodiment, the zone is generally rectangular or square shaped. If the occupant's center of gravity is outside of the zone, controller 58 issues an alert at step 1226. If the occupant's center of gravity is not outside of the zone, controller 58 proceeds to step 1212, which is essentially the same as step 1204, where the controller 58 determines whether an obstruction is present based on the obstruction sensors 61, and if it is activates an obstacle alert at step 1222, and then disarms the bed exit system at step 1224.

If no obstruction is present, controller 58 proceeds to step 1216 (FIG. 11). At step 1216, controller 58 determines whether any of the initial values acquired at step 1208 have changed during the interim between step 1208 and step 1216. More specifically, in the illustrated embodiment, controller 58 determines at step 1216 whether any of the following values have changed: the value of pivot angle 70, the position value (e.g. up, down, and/or intermediate) for each of the siderails 36, the value of tilt angle 72, the value of turn angle 74, the height value 78, and the position value corresponding to the current relative longitudinal position of support deck 30 on litter frame 28. Controller 58 determines these values at step 1216 based upon readings from the pivot sensor 66*a*, siderail sensor 66*b*, tilt sensor 66*c*, turn sensor 66*d*, height sensor 66*e*, and position sensor 66*f*, respectively.

If none of these values have changed since the values were initially taken at step 1208, controller 58 proceeds to step 1210, described above. If controller 58 determines at step 1216 that one or more of the initial values (from step 1208) have changed, it proceeds to a step 1218, where it determines one or more compensation factors that correspond to the changed values. That is, for every value that has changed, controller 58 computes a compensation factor at step 1218. Thus, for example, if pivot angle 70 and height 78 are both different at step 1218 than they were initially at step 1208, controller 58 computes a pivot angle compensation factor and a height compensation factor. In general, controller 58 calculates at step 1218 one or more compensation factors that provide an estimate of how much the center of gravity reading taken at step 1218 has been influenced by factors other than the occupant moving relative to support deck 30.

Once compensation factors are calculated, the controller 58 can proceed to step 1220 where it applies the compensation factor(s) to the center of gravity computed at step 1206. The result is a center of gravity calculation that has substantially eliminated changes in the center of gravity due to movement of one or more components of person support apparatus 20, or other effects that are not the result of the occupant changing his or her weight distribution relative to support deck 30 or support surface 31. Consequently, the compensated center of gravity calculation made at step 1220 corresponds substantially to the occupant's center of gravity. Controller 58 then proceeds to step 1210 where it determines whether the occupant's center of gravity (i.e. the compensated center of gravity calculated at step 1220) is inside or outside of the zone that defines the exit alert conditions. If it is outside the zone, an alert is issued at step 1226. If it inside the zone, no alert is issued and—to the extent exit detection system 56 has not been shut off—control returns to step 1212 where the system checks whether an obstruction has been encountered. The manner in which controller 58 determines and applies the compensation factors at steps 1216, 1218, and 1220 may be carried out in the manners disclosed in commonly assigned U.S. patent publication 2020/0214599 filed by Kostic et al. and entitled EXIT DETECTION SYSTEM WITH COMPENSATION, the complete disclosure of which is incorporated herein by reference in its entirety. Alternatively, controller 58 may be modified to not calculate and/or apply any of the compensation factors of steps 1216, 1218, and 1220, but instead skip these steps.

It will be understood that, although not illustrated in FIG. 11, algorithm 1200, in at least some embodiments, includes the additional step of automatically re-arming exit detection system 56 when the obstruction is no longer detected. That is, after disarming exit detection system 56 in response to the detection of contact with an obstacle, controller 58 repetitively checks to see if contact with that obstacle persists. If it continues to persist, it continues to leave exit detection system disarmed. If the obstruction is removed and/or one or more components of person support apparatus 20 are moved so that contact with the obstruction no longer persists, controller 58 is configured to automatically re-arm exit detection system 56.

It will also be understood that algorithm 1200 may be modified to automatically send a message via network transceiver 73 to a server coupled to the healthcare facility's local area network as part of step 1224. The message indicates that exit detection system 56 has been disarmed. Thus, in addition to disarming exit detection system 56 in response to detecting an obstacle, controller 58 may be configured to automatically send a message notifying a remote server that it has automatically disarmed the exit detection system 56. Still further, if controller 58 is configured to automatically re-arm exit detection system 56 when the obstacle is no longer detected, controller 58 may be further configured to automatically send a message to the server via network transceiver 73 indicating that exit detection system 56 has been re-armed. The server that receives these messages may be a server that executes a caregiver assistance application of the type disclosed in commonly assigned PCT patent application PCT/US2020/039587 filed Jun. 25, 2020, and entitled CAREGIVER ASSISTANCE SYSTEM, the complete disclosure of which is incorporated herein by reference.

Figure 12:
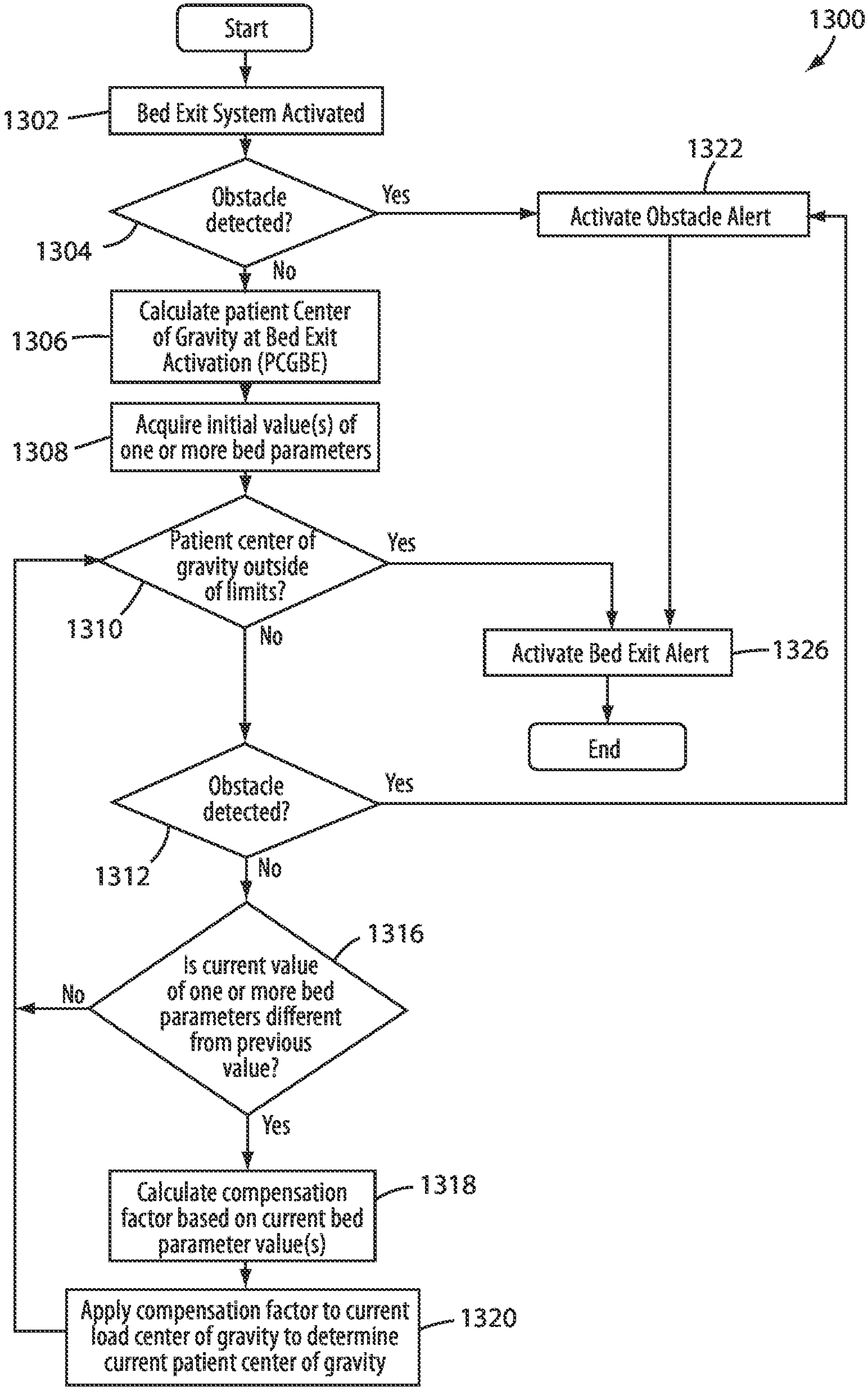
FIG. 12 is a flowchart of an alternative embodiment of an exit detection algorithm that can be carried out by the exit detection system of the person support apparatus.

In an alternative embodiment, instead of automatically deactivating (i.e. disarming) exit detection system 56 in response to an obstacle being detected, the exit detection system 56 can be configured to automatically issue an exit detection alert in response to detecting contact with an obstacle. One example of such an embodiment is shown in FIG. 12. FIG. 12 illustrates an exit detection algorithm 1300 that is carried out, in at least one embodiment, by controller 58 of exit detection system 56. Exit detection algorithm 1300 begins at an initial step 1302 when exit detection system 56 is armed. After being armed at step 1302, controller 58 proceeds to step 1304 where the controller 58 is configured to determine whether an obstruction is being encountered. If an obstruction is present, the bed exit detection system 56 is configured to activate an obstacle alert at step 1322. From step 1322, controller 58 proceeds to step 1326 where it activates the exit alert of the exit detection system 56.

In some modified embodiments, algorithm 1300 may be modified to omit step 1322 and skip directly from step 1304 to step 1326 when an obstacle is detected. In such modified embodiments, controller 58 does not issue a separate obstruction alert when an obstruction is detected and exit detection system 56 is armed, but instead only issues an exit alert. Further, in such modified embodiments, if exit detection system 56 is not armed and obstruction detection sensor 61 detects contact with an obstruction, controller 58 is configured to issue an obstruction detection alert. Thus, in such embodiments, controller 58 is configured to issue an exit detection alert when exit detection system 56 is armed and an obstruction is contacted, and to issue an obstruction alert when exit detection system 56 is disarmed and an obstruction is contacted.

It will be understood that the difference between an exit alert and an obstruction alert may take on a variety of different forms. In general, an exit alert will always be communicated to a nurse call system of the healthcare facility via the nurse call interface 67 that is built into person support apparatus 20. When nurse call interface 67 is coupled to the nurse call system via a cable, the communication of the exit alert to the nurse call system typically takes place by opening or closing one or more relays within nurse call interface 67 that are in electrical communication with corresponding pins of a nurse call outlet built into a headwall of the healthcare facility. When nurse call interface 67 is coupled to the nurse call system via wireless communication, the communication of the exit alert to the nurse call system may take place by sending a wireless signal to a wall mounted headwall module that, in response, opens or closes one or more relays that are in electrical communication with the pins of the nurse call outlet. Further details of the manners in which the nurse call interface 67 may communicate an exit alert to the nurse call system, whether via a cable or wirelessly, are disclosed in the following commonly assigned U.S. patent applications: Ser. No. 62/896,075 filed Sep. 5, 2019 by Alexander Bodurka et al. and entitled PATIENT SUPPORT APPARATUSES WITH NURSE CALL CONNECTION DETECTION; Ser. No. 15/945,437 filed Apr. 4, 2018, by inventors Krishna Bhimavarapu et al. and entitled PATIENT SUPPORT APPARATUSES WITH RECONFIGURABLE COMMUNICATION; Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION; Ser. No. 16/215,911 filed Dec. 11, 2018, by inventors Alexander Bodurka et al. and entitled HOSPITAL HEADWALL COMMUNICATION SYSTEM; Ser. No. 62/833,943 filed Apr. 15, 2019, by inventors Alexander Bodurka et al. and entitled PATIENT SUPPORT APPARATUSES WITH NURSE CALL AUDIO MANAGEMENT; Ser. No. 16/215,911 filed Dec. 11, 2018, by inventors Alexander Bodurka et al. and entitled HOSPITAL HEADWALL COMMUNICATION SYSTEM; Ser. No. 16/217,203 filed Dec. 12, 2018, by inventor Alexander Bodurka, and entitled SMART HOSPITAL HEADWALL SYSTEM; and Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosures of all of which are incorporated herein by reference.

In some embodiments of person support apparatus 20, the exit alert is also communicated wirelessly via a separate communication channel to one or more servers. In such embodiments, controller 58 is configured to utilize network transceiver 73 to transmit a notification to a server on the local area network of the healthcare facility. This notification indicates that an exit alert has been issued. In some embodiments, the server may forward this notification to one or more portable electronic devices carried by one or more caregivers associated with the healthcare facility. Alternatively, or additionally, the exit detection alert may be forwarded to one or more servers that are located remotely from the healthcare facility and that are not part of the healthcare facility's local area network. Such forwarding may take place over an Internet gateway, router, or other conventional network appliance that communicatively couples the local area network to the Internet.

In some embodiments, the obstruction detection alert is only a local alert that involves one or more of a sound or light emitted from person support apparatus 20. Additionally, such localized alerting may involve displaying a message on an electronic display of person support apparatus. The message may indicate that an obstruction was detected. In some embodiments, controller 58 may also be configured to send a notification message to a server on the healthcare facility's network indicating that an obstruction was detected. This obstruction notification message may be forwarded to one or more other servers and/or one or more portable electronic devices carried by one or more caregivers. The obstruction alert is not issued through the nurse call interface 67 because conventional nurse call outlets do not include a pin (or set of pins) that are able to communicate this information. However, if person support apparatus 20 is coupled to a nurse call system that is capable of communicating this information, controller 58 may be configured to also send the obstruction alert through nurse call interface 67.

In those embodiments where controller 58 transmits the obstruction alert and/or the exit alert via network transceiver 73 to a server of the local area network, the server may be a server the executes a caregiver assistance application of the type disclosed in commonly assigned PCT patent application PCT/US2020/039587 filed Jun. 25, 2020, and entitled CAREGIVER ASSISTANCE SYSTEM, the complete disclosure of which is incorporated herein by reference. In such embodiments, the caregiver assistance system may then forward the exit alert and/or obstruction detection alert to designated portable electronic devices (and/or stationary electronic devices) so that caregivers associated with those devices are apprised of the obstruction detection and/or the exit alert.

In some embodiments of person support apparatus 20, controller 58 is configured to send an exit alert message to a remote server via network transceiver 73 when an obstruction is detected, but to include information within the notification message indicating that the exit alert is due to an obstruction being detected, not due to the occupant exiting from person support apparatus 20. In this manner, any messages forwarded by the server to portable electronic devices carried by healthcare personnel will be informed that the exit alert is being caused, not by an occupant exit, but rather by an obstruction that was encountered.

Returning to FIG. 12 and algorithm 1300, if no obstruction is detected at step 1304, the system proceeds through steps 1306, 1308, 1310, 1312, 1316, 1318, and 1320, which are the same as, except as noted below, steps 1206, 1208, 1210, 1212, 1216, 1218, and 1220, respectively, of algorithm 1200, and which therefore need not be described again. The only step of this set of steps of algorithm 1300 that differs from the corresponding set of steps of algorithm 1200 is step 1312. At step 1312, if obstruction detection sensor 61 detects an obstacle, controller 58 proceeds to step 1326 of algorithm 1300, where it issues an exit detection alert. This is slightly different from step 1212 of algorithm 1200 where controller 58 proceeds, when an obstruction is detected, to steps 1222 and 1224 where it issues an obstruction alert and disarms exit detection system 56.

It will be understood that, although not illustrated in FIG. 12, algorithm 1200, in at least some embodiments, includes the additional step of automatically deactivating the exit alert when the obstruction is no longer detected. That is, after activating the exit alert in response to the detection of contact with an obstacle, controller 58 repetitively checks to see if contact with that obstacle persists. If it continues to persist, it continues to issue the exit alert. If the obstruction is removed and/or one or more components of person support apparatus 20 are moved so that contact with the obstruction no longer persists, controller 58 is configured to automatically terminate the exit alert, in at least some embodiments. This automatic termination may take place substantially immediately after the obstruction is no longer detected (e.g. within a second or two), or it may take place after a predetermined delay period expires. In some embodiments, the predetermined time period may be configurable by the user.

Figure 13:
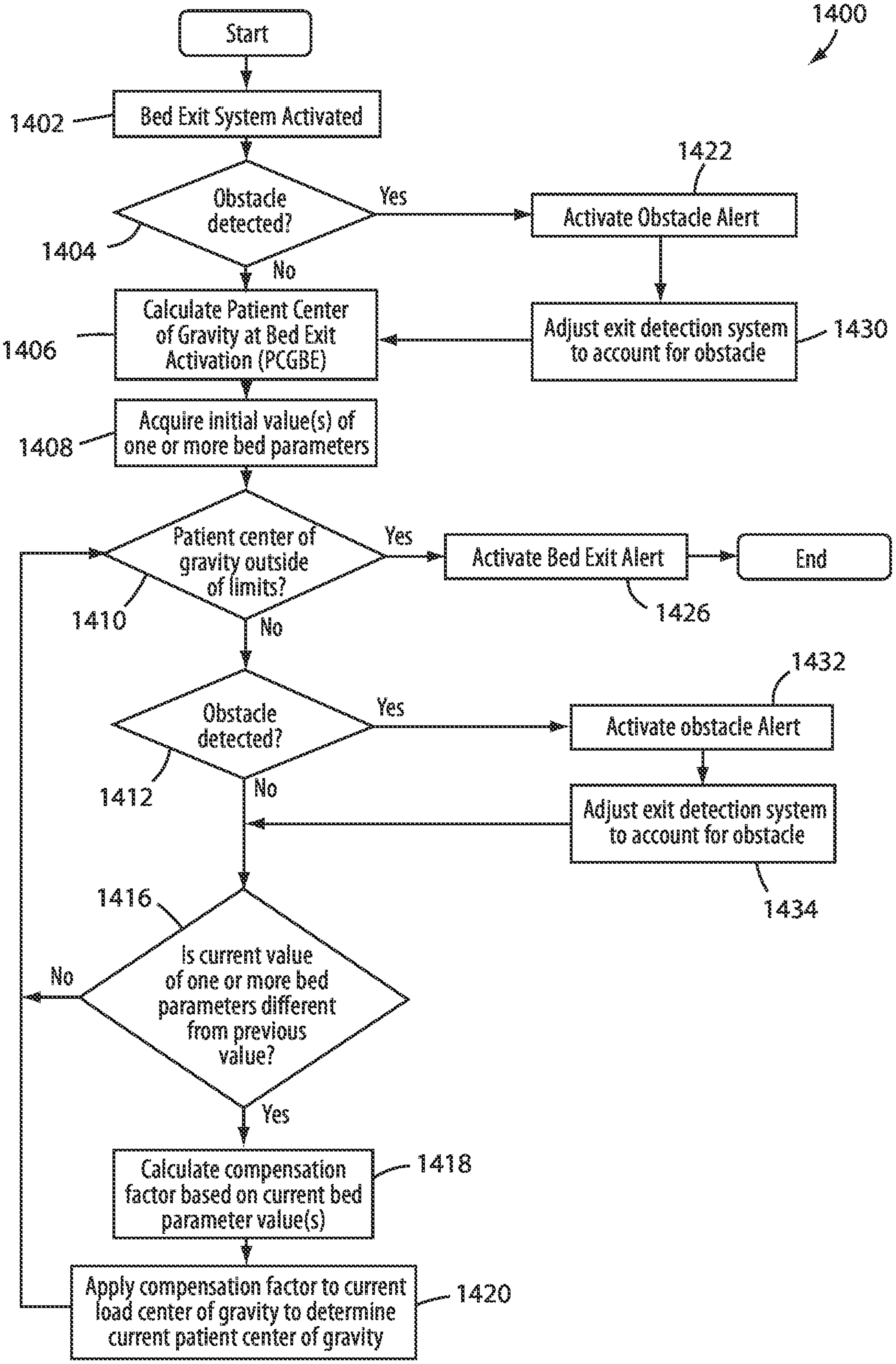
FIG. 13 is a flowchart of yet another alternative embodiment of an exit detection algorithm that can be carried out by the exit detection system of the person support apparatus.

In other embodiments, the exit detection system 56 is configured to react to obstruction detection by compensating for the errors introduced into the load cell readings by the obstruction so that the bed exit system can continue to operate in an accurate manner despite the obstruction. In an example of one such exit detection system, controller 58 is configured to execute an exit detection algorithm 1400 as illustrated in FIG. 13. Exit detection algorithm 1400 begins at an initial step 1402 when exit detection system 56 is armed, such as by a user manipulating one or more controls on user interface 62. From step 1402, controller 58 proceeds to step 1404 where it checks the outputs from the one or more obstruction detectors onboard person support apparatus 20 (e.g. 61, 161, and/or other(s)) to see if contact has been made with an obstruction. If such contact is detected by any one or more of the obstruction detection sensors, controller 58 proceeds to step 1422 where it issues an obstruction alert. The obstruction alert is the same type of obstruction alert issued in the other algorithms 1200 and/or 1300 discussed above.

From step 1422, controller 58 proceeds to step 1430 where it makes adjustments to the operation of exit detection system 56 that are designed to account for the force components detected by force sensors 60 that are due to contact with the obstacle. In other words, at step 1430, controller 58 makes adjustments to the operation of exit detection system 56 that are designed to either remove or accommodate the errors introduced into the calculation of the occupant's center of gravity that are due to the obstruction exerting forces on one or more of the force sensors 60. As will be discussed in greater detail below, controller 58 may be configured to implement step 1430 in a variety of different manners.

Figure 14A:
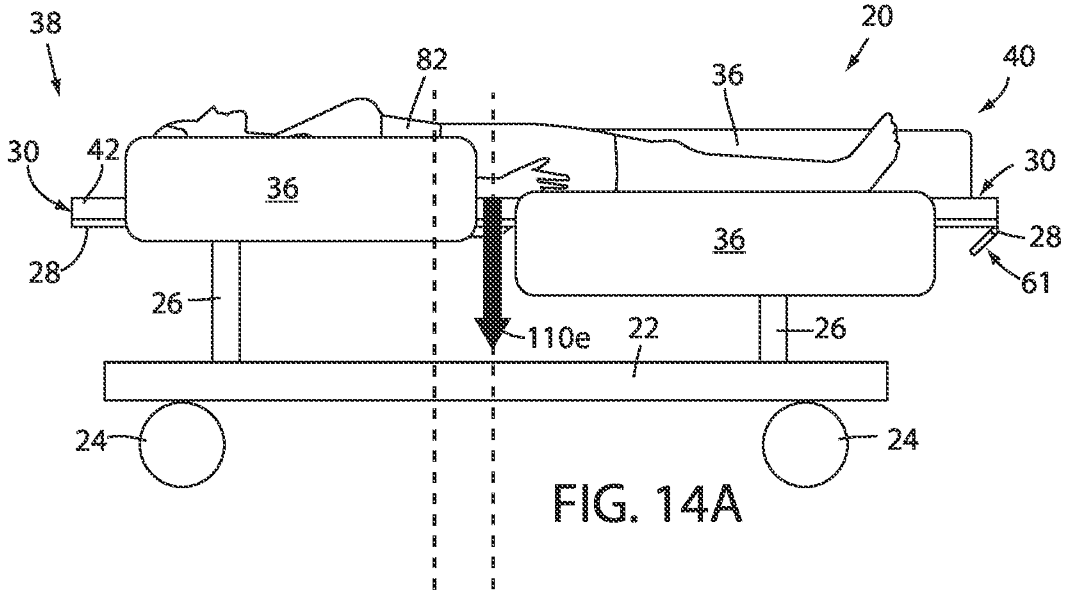
FIG. 14A is a side view of the person support apparatus illustrating a center of gravity of an occupant when no obstacle is detected by an obstruction sensor onboard the person support apparatus.
Figure 14B:
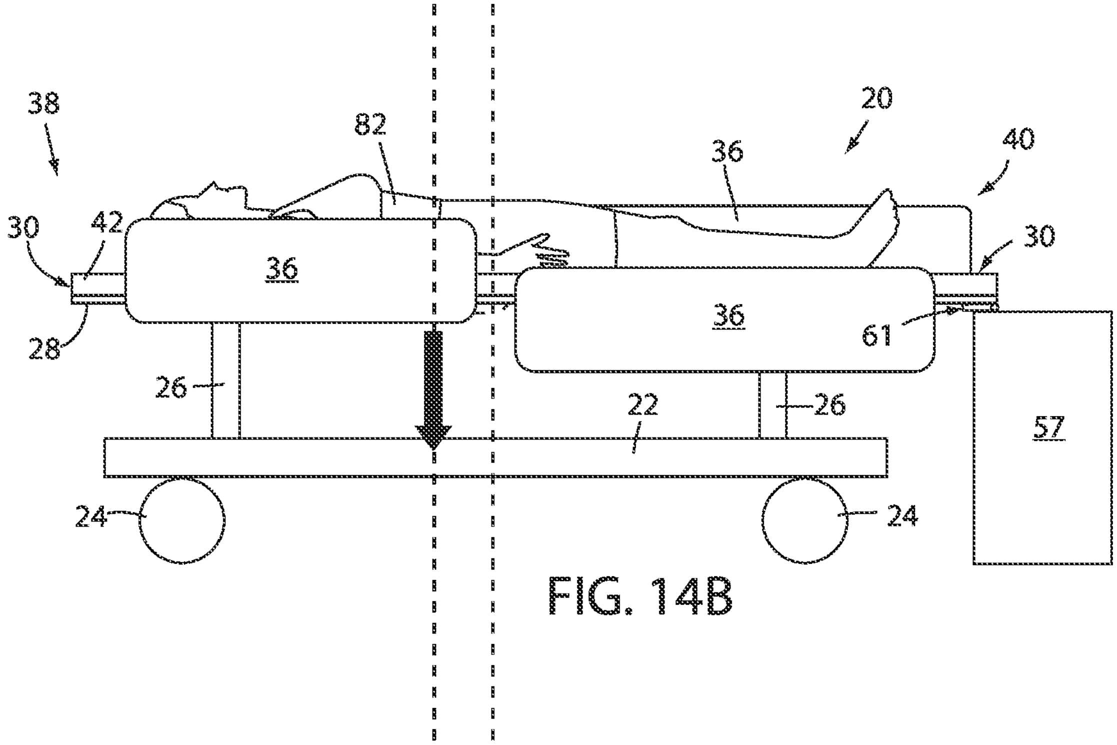
FIG. 14B is a side view of the person support apparatus illustrating a changed center of gravity of the occupant after an obstacle has been detected by the obstruction sensor.
Figure 14C:
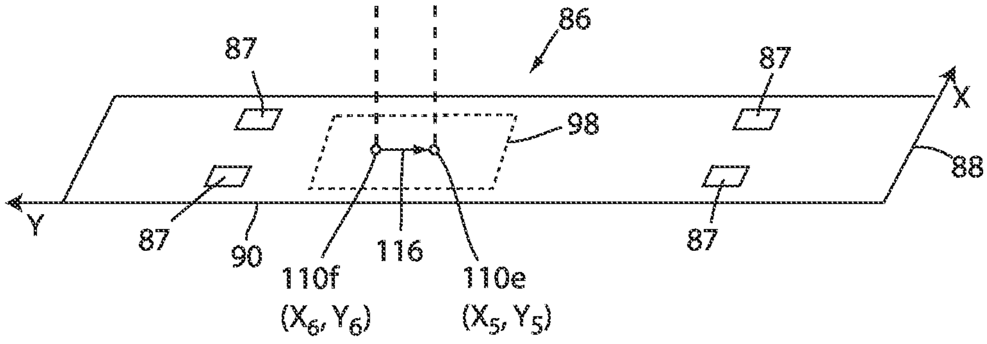
FIG. 14C is a coordinate frame of reference illustrating a first type of compensation that may be applied by the exit detection system to account for the difference between the calculated centers of gravity of FIGS. 14A and 14B.

In a first manner, which is illustrated in more detail in FIGS. 14A-C, controller 58 is adapted to adjust the operation of exit detection system 56 by shifting the calculated center of gravity of the occupant such that the effects of the obstruction on the readings from the force sensors 60 are removed. In a second manner, which is illustrated in greater detail in FIGS. 15A-C, controller 58 is adapted to adjust the operation of exit detection system 56 by changing one or more thresholds that controller 58 compares the processed outputs of the force sensors 60. For example, in those embodiments of exit detection system 56 in which controller 58 compares the occupant's center of gravity to a zone (and issues an exit alert if the center of gravity is outside of the zone), controller 58 may adjust the size, shape, and/or location of the zone in response to the detection of an obstacle. In other embodiments, such as where exit detection system 56 does not use zones, but instead compares ratios of force sensor 60 outputs, controller 58 may be configured to change the thresholds that such ratios are compared to, as will be discussed in greater detail below. In a third manner, controller 58 may be configured to combine the adjustments illustrated in FIGS. 14A-C with the adjustments illustrated in FIGS. 15A-C such that it both adjusts the center of gravity calculations and changes the size, shape, and/or location of one or more zones. Each of these different manners of responding to an obstruction are discussed in more detail below.

Turning to the first manner by which controller 58 may adjust the operation of exit detection system 56 at step 1430 of algorithm 1400 (FIG. 13), controller 58 is adapted to continuously record the outputs of force sensors 60 during operation of person support apparatus 20. These recordings, which are typically taken multiple times a second, are stored in a memory accessible to controller 58 and may be discarded after a certain amount of time has elapsed without an obstruction being detected. When an obstruction is detected, controller 58 automatically marks a first set of stored force outputs that were taken immediately prior to the obstruction being detected, as well as a second set of outputs that are taken immediately after the obstruction is detected. The number of recordings in the first and second sets may vary, but in at least one embodiment, about one second's worth of force recordings before the obstruction is detected are marked for the first set, and about one second's worth of force recording immediately after the obstruction is detected are marked for the second set.

Once the two sets of readings are identified, controller 58 determines the difference between the two, such as by determining the average of the first set, determining the average of the second set, and then subtracting one from the other. Other processing may also or alternatively be used in order to compute the general difference between the first and second sets of readings. The purpose of the two sets of readings is to capture the difference in the outputs of the force sensors immediately prior to the obstruction detection and immediately after the obstruction detection. This difference is presumed to be due to the obstruction.

When calculating this difference, it will be understood that controller 58 does this for each load cell (force sensor 60). That is, controller 58 identifies a first set of readings for the right head end load cell that were captured immediately before the obstruction was detected and identifies a second set of readings for the right head end load cell that were taken by the right head end load cell immediately after the obstruction was detected. The difference between these two sets is then determined and stored as a right head end load cell adjustment factor. This same process is repeated for the other load cells: the left head end load cell, the right foot end load cell, and the left foot end load cell. The result is the generation of four load cell adjustment factors—one for each of the four load cells. Controller 58 then applies each of these load cell adjustment factors to the outputs from each of the corresponding load cell readings that are taken after the obstruction is detected (and continues to apply these adjustment factors until the obstruction is no longer detected—at which point is stops applying these adjustment factors). This process is better explained with reference to FIGS. 14A-C.

FIG. 14A illustrates person support apparatus 20 when no obstructions are being detected by any of its obstruction detection sensors 61 (and/or 161 and/or others). In this situation, controller 58 calculates a no-obstruction center of gravity 110*e* that, as shown in FIG. 14C, is located in a frame of reference 86 at location ($X_5$, $Y_5$). If litter frame 28 is lowered until it comes into contact with an obstruction detection sensor 61, such as shown in FIG. 14B, the contact between obstruction 57 and litter frame 28 will change the outputs of at least one of, and likely all four of, the force sensors 60. As a result, when controller 58 calculates a new center of gravity after the obstruction is detected (an after-obstruction center of gravity 110*f*), it can be seen in FIG. 14C that the after-obstruction center of gravity 110*f* has shifted toward the head end 38 of person support apparatus 20. Specifically, in the frame of reference 86, the after-obstruction center of gravity 110*f* is now located at ($X_6$, $Y_6$). This shift is due to a portion of the weight of litter frame 28 (and the objects supported thereon) being supported by obstruction 57. As a result of this partial support, the load cells positioned at the foot end of person support apparatus 20 will experience a decrease in the forces they sense (and the head end load cells may also experience a decrease in force outputs, but their decrease will be smaller due to their greater distance from the obstruction 57). As a result of the forces sensed by the foot end load cells decreasing, the calculated center of gravity 110*f* shifts toward the head end 38 of person support apparatus 20.

As shown in FIG. 13, a vector 116 extends between centers of gravity 110*e* and 110*f* and corresponds to an obstruction compensation factor that can be used to compensate for the change in weight distribution due to the litter frame 28 contacting obstruction 57. In some embodiments, controller 58 may be configured to calculate this vector and apply it to all subsequent center of gravity calculations for as long the obstruction is detected. In other embodiments, controller 58 may be configured to account for this vector without explicitly calculating it, and/or in other manners. For example, in one manner mentioned above, controller 58 is configured to store a first set of load cell readings from each load cell prior to the obstruction being detected. These load cell readings correspond to the readings used to calculate the no-obstruction center of gravity 110*e*. After the obstruction is detected, controller 58 may then take a second set of load cell readings, compare them to the load cell readings used to calculate the no-obstruction center of gravity 110*e*, determine the differences, and then subtract those differences from all future load cell readings that are taken while the obstruction remains in contact with person support apparatus 20.

Thus, for example, if the readings from the four load cells immediately before an obstruction is encountered (or an average of multiple readings taken immediately before the obstruction is detected) are 25, 30, 37, and 22 pounds, and the readings from these same four load cells (or an average of multiple readings) taken after the obstruction is detected are 20, 25, 40, and 25, respectively, controller 58 will compute the following four differences: (1) −5.0 (20−25); (2) −5.0 (25−30); (3) 3.0 (40−37); and (4) 3.0 (25−22). As a result, controller 58 will, in at least one embodiment, add five pounds to all subsequent readings of the first and second load cells and subtract three pounds from all subsequent readings from the third and fourth load cells. The result will be that the subsequently calculated center of gravities will have the changes in the force readings that occurred between the first and second sets of load cell readings (i.e. during the time of the impact with the obstruction) removed from the subsequent calculations. The subsequently calculated center of gravities will therefore be a more accurate reflection of the occupant's actual center of gravity on person support apparatus 20. As noted, the subtraction of these compensation values from each of the load cells (e.g. −5.0, −5.0, 3.0, and 3.0) will continue until the obstruction is no longer detected.

As was noted above in the discussion of step 1430 of algorithm 1400 (FIG. 13), controller 58 may alternatively be configured to adjust the exit detection system operation in a manner different from that just described. Specifically, instead of adjusting the load cell readings taken after the obstruction is detected by the load cell compensation factors discussed above, controller 58 may alternatively be configured to make no adjustments to the load cell readings after the obstruction is detected, but instead may make one or more changes to the size, shape, and/or position of the alert zone 98. This alternative method of adjusting the operation of exit detection system 56 is better understood with reference to FIGS. 15A-C.

Figure 15A:
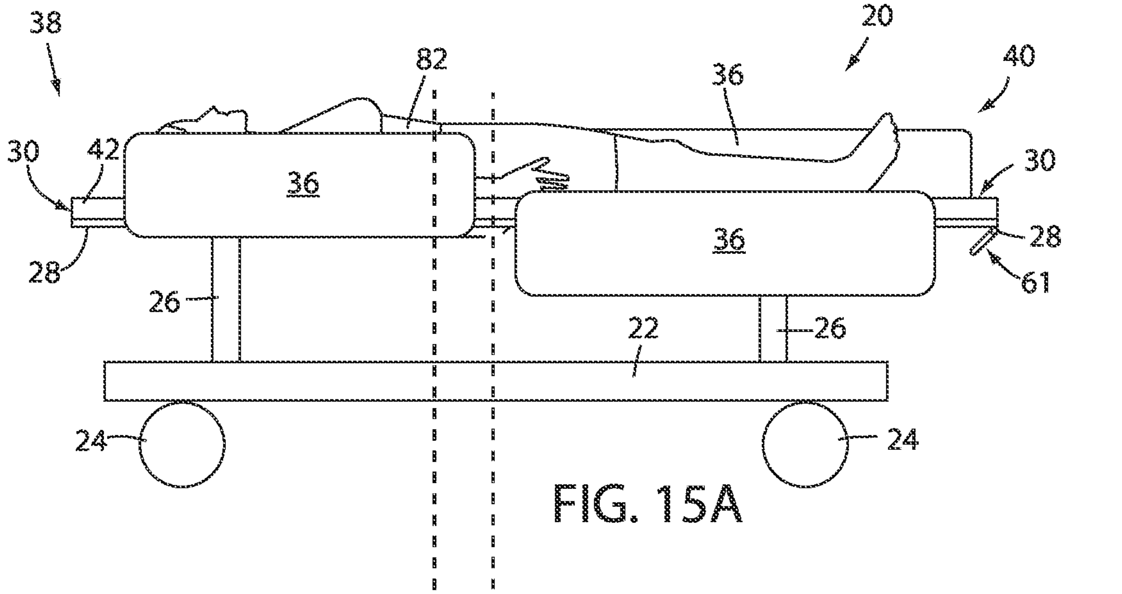
FIG. 15A is a side view of the person support apparatus illustrating a center of gravity of the occupant when no obstacle is detected by an obstruction sensor onboard the person support apparatus.

FIG. 15A, like FIG. 14A, depicts a person support apparatus 20 when no obstruction is being detected. As seen in FIG. 15C, the center of gravity of the occupant in this situation is no-obstruction center of gravity 110*e* (FIG. 15C), which is defined by coordinates ($X_5$, $Y_5$) in frame of reference 86. If litter frame 28 is lowered from the position shown in FIG. 15A to the position shown in FIG. 15B in which an obstruction 57 has contacted obstruction detection sensor 61, the center of gravity calculated by controller 58 will change to the after-obstruction center of gravity 110*f* shown in FIG. 15C. However, rather than adjusting the load cell readings taken after the obstruction is detected, as was described above with respect to FIGS. 14A-C, controller 58 is adapted in the embodiment illustrated in FIGS. 15A-C to adjust the alert zone 98. Thus, as can be seen in FIG. 15C, controller 58 uses alert zone 98 prior to the obstruction being detected, and then switches to using alert zone 198 after the obstruction is detected. Controller 58 then continues to use alert zone 198 until the obstruction is no longer detected.

As was described previously, controller 58 uses alert zone 98 (or 198) to compare the currently calculated center of gravity of the occupant. If the current center of gravity of the occupant travels outside the boundaries of alert zone 98 (or 198) while the exit detection system 56 is armed, controller 58 issues an exit alert.

Returning to FIG. 14B, when litter frame 28 is lowered in the manner shown therein until it contacts obstruction 57, the contact between litter frame 28 and obstruction 57 will cause some of the weight supported by the foot end load cells to be off-loaded onto the obstruction 57. (Some of the weight supported by the head end load cells may also be off-loaded, but this weight will be smaller because the obstruction impacts litter frame 28 closer to foot end 40 than head end 38. As a result of the offloading of a portion of the weight of litter frame 28 (and the items supported thereon, including the occupant), the outputs from the head end load cells will decrease. This reduction in the force readings from the head end load cells will result in a shift of the patient's calculated center of gravity toward head end 38. However, this shift in the patient's calculated center of gravity will be due to the contact with obstruction 57, not due to an actual movement of the patient toward head end 38. In other words, the obstruction will cause an error to be introduced into the calculation of the occupant's center of gravity.

Figure 15B:
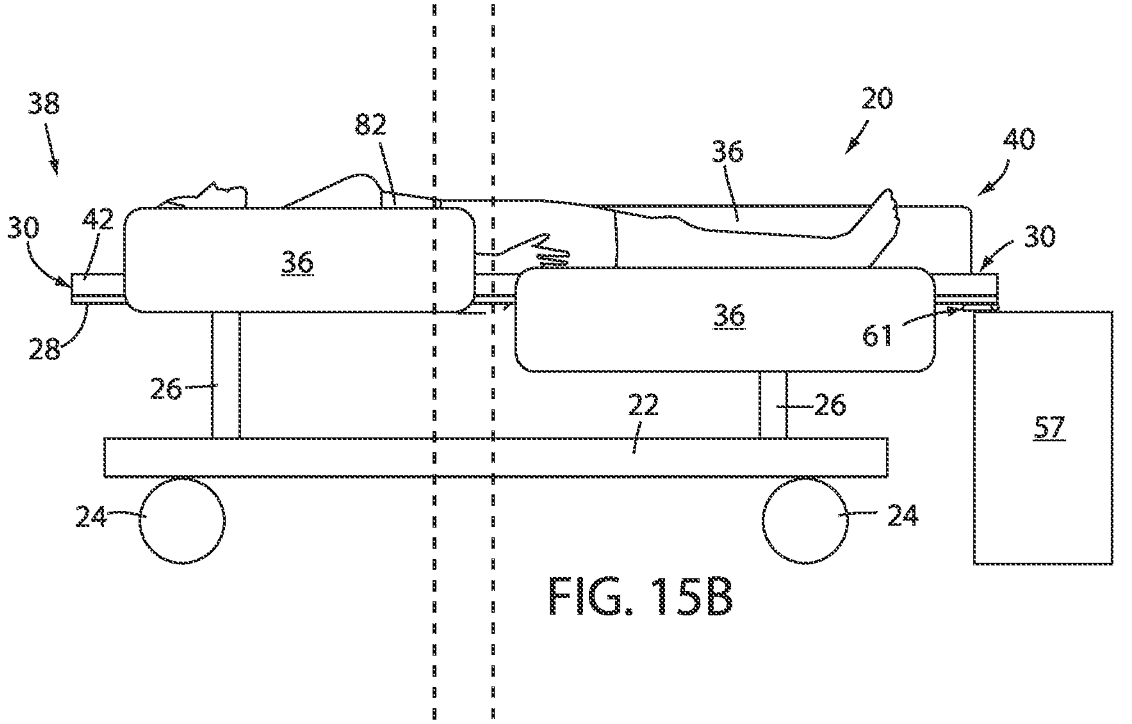
FIG. 15B is a side view of the person support apparatus illustrating a changed center of gravity of the occupant after an obstacle has been detected by the obstruction sensor.
Figure 15C:
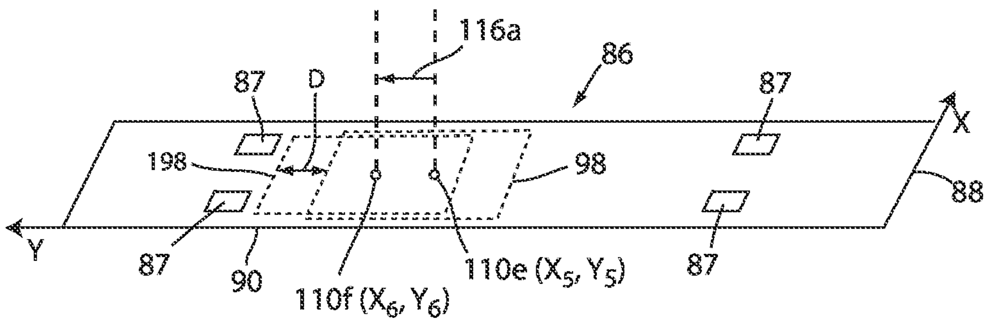
FIG. 15C is a coordinate frame of reference illustrating a second type of compensation that may be applied by the exit detection system to account for the difference between the calculated centers of gravity of FIGS. 15A and 15B.

In the embodiment of FIGS. 15A-C, the controller 58 compensates for this error changing one or more of the size, shape, and/or location of the boundary the alert zone 98 in response to contact with obstruction 57. In some such embodiments, such as the one shown in FIG. 15C, controller 58 may be configured to shift the location of alert zone 98 toward head end 38 40 without changing the size and/or shape of zone 98. In other embodiments, controller 58 may be configured to elongate (change the shape of) zone 98 so that it extends toward head end 38 a greater distance (but may continue to extend toward foot end 40 the same amount). In still other embodiments, controller 58 may be configured to make other adjustments to the size, shape, and/or position of the boundary of zone 98.

In some embodiments, such as the one shown in FIG. 15C, controller 58 is configured to take into account the amount of force off-loaded onto obstruction 57 and make different adjustments to alert zone 98 based on the differing amounts of off-loaded force. In these embodiments, controller 58 is configured to determine the value of vector 116*a*. This may be done by determining the difference between the calculated center of gravity immediately before the obstruction was detected and the calculated center of gravity immediately after the obstruction was detected. This vector 116*a* value is then added to all points on the boundary of alert zone 98, resulting in the shifted zone 198, which is shifted from zone 98 by the same amount and direction as vector 116*a*. That is, the distance D between zones 98 and 198 is equal to the magnitude of vector 116*a*.

In some alternative embodiments (not shown), controller 58 may be configured to make the same changes to the size, shape, and/or location of alert zone 98 regardless of the amount of force that is offloaded from load cells 54 to obstruction 57. That is, regardless of whether or not litter frame 28 exerts, say, ten pounds of force onto obstruction 57 or twenty pounds, controller 58 is configured to change the size, shape, and/or location of alert zone 98 in the same manner for these differing amounts of force. In some of these alternative embodiments, controller 58 may be configured to automatically switch to using a different alert zone 98 having a different sensitivity in response to the detection of an obstacle. For example, in some embodiments of exit detection system 56, a user is able to select a different sensitivity level, which may correspond to the general size of a zone 98. In such embodiments, controller 58 may be configured to automatically switch to using, for example, the zone 98 with the least sensitivity in response to detecting an obstruction.

In still other embodiments, controller 58 may be configured to automatically switch to using a non-zone based exit detection algorithm in response to the detection of an obstruction. For example, in at least one embodiment, controller 58 is configured to stop comparing a calculated center of gravity to an alert zone in response to the detection of an obstacle, and instead to look for a drop in total weight detected on litter frame 28 of more than a predefined threshold (which may be expressed in absolute terms (e.g. pounds), or as a percentage of the total current weight or as a percentage of the occupant's weight). In any of the aforementioned embodiments, when the obstacle is no longer detected, controller 58 may be configured to automatically switch back to using the algorithm and/or zone it was using prior to contact with the obstacle (and/or switch back to not using a compensation factor).

In those embodiments of person support apparatus 20 that include multiple obstruction sensors 61, 161, controller 58 may be configured to react in different manners depending upon which obstruction sensor 61, 161 detects contact with an obstruction 57. For example, in some embodiments, if a first obstruction sensor 61 positioned toward the foot end of litter frame 28 detects contact with an obstruction 57 as the litter frame is lowered onto the obstruction 57, controller 58 may be configured to adjust the size, shape, and/or position of the alert zone 98 in a manner that at least partially shifts the zone 98 toward head end 38. As noted, this adjustment may take into account the magnitude of the off-loaded force, or it may be insensitive to the amount of force off-loaded onto the obstruction. On the other hand, if a second obstruction sensor is positioned at, say, head end 38 of litter frame 28 and this second obstruction sensor detects as obstruction 57 as litter frame 28 is lowered onto the obstruction, controller 58 may be configured to adjust the size, shape, and/or position of the alert zone 98 in a manner that at least partially shifts the zone 98 toward foot end 40. This adjustment may also take into account the magnitude of the off-loaded force, or it may be insensitive to the amount of force off-loaded onto the obstruction. Regardless of whether or not the magnitude of the offloaded force is determined or not, the adjustments to zone 98 may be different, depending upon which one of the first or second obstruction sensors detects contact with the obstruction. The same is true for any other sensors that may be added to person support apparatus 20 beyond the aforementioned first and second obstruction sensors 61, such as one or more obstruction sensors that are positioned along the side(s) of person support apparatus 20 (and which may prompt exit detection system 56 to change the size, shape, and/or location of zone 98 in a lateral manner).

Returning to algorithm 1400 and FIG. 13, after making the adjustments to the operation of exit detection system 56 at step 1430 in one of the manners (or a combination of both) illustrated in FIGS. 14A-C or FIGS. 15A-C, controller 58 moves to steps 1406, 1410, 1412, 1416, 1418, and 1420, which are the same as, except as noted below, steps 1206, 1208, 1210, 1212, 1216, 1218, and 1220, respectively, of algorithm 1200, and which therefore need not be described again. The only step of this set of steps of algorithm 1400 that differs from the corresponding set of steps of algorithm 1200 is step 1412. At step 1412, if obstruction detection sensor 61 (and/or 161) detects an obstacle, controller 58 proceeds to step 1432 of algorithm 1400, where it activates an obstacle detection alert and then proceeds to step 1434. At step 1434, controller 58 adjusts the operation of exit detection system 56 to account for the influence of the obstruction on the exit detection system. Step 1434 is the same as step 1430, which was previously described above, and may be carried out in different manners, as was discussed. After the appropriate adjustments are made at step 1434, controller 58 returns to step 1416 and continues to steps 1418, 1420, and so on, in the manner previously described.

It will be understood that, although not illustrated in FIG. 13, algorithm 1400, in at least some embodiments, includes the additional step of automatically removing the adjustments made at steps 1430 and/or 1434 when the obstruction is no longer detected. That is, after implementing the adjustments at these steps, controller 58 repetitively checks to see if contact with that obstacle persists. If it continues to persist, it continues to adjust the current load cell readings and/or size, shape, and/or location of the alert zone 98. If the obstruction is removed and/or one or more components of person support apparatus 20 are moved so that contact with the obstruction no longer persists, controller 58 is configured to automatically terminate these adjustments to the load cell readings and/or the alert zone 98.

It will be understood that in any of the embodiments of exit detection system 56 that utilize any of algorithms 1200, 1300, or 1400 (or other algorithms), exit detection system 56 may be configured to allow a user to select which zone will be used by controller 58 when determining whether to issue an alert or not. That is, exit detection system 56 may include multiple alert zones 98 of different sizes, shapes, and/or locations, and allow the user to select which zone to utilize, thereby allowing the user to select different sensitivity levels for exit detection system 56. In some embodiments, person support apparatus 20 includes three predefined zones and is adapted to allow a user to select which one of these three zones is to be used at a given time via user interface 62. In other embodiments, a different numbers of zones are permitted by exit detection system 56.

It will also be understood that in any of the embodiments of exit detection system 56 that permit the user to select from multiple alert zones 98, controller 58 may be configured to define the different alert zones 98 in different manners. For example, in one embodiment, the zone having the smallest area (in coordinate system 86) has its boundaries defined using the patient's first center of gravity reading taken by exit detection system 56. That is, the smallest zone is centered at whatever location the person's center of gravity is initially located. The zone having the largest area is defined, in at least one embodiment, without regard to the occupant's initial location, but instead has fixed values in coordinate system 86. For example, in one embodiment, the zone with the largest area has its edges located just inwardly from the outer edges of support deck 30. Other manners of defining the zone boundaries may also be used.

Still further, it will also be understood that, in any of the embodiments of exit detection system 56 that utilize any of algorithms 1200, 1300, or 1400 (or other algorithms), exit detection system 56 may be configured to dynamically change the size, shape, and/or location of the alert zones based on factors other than the detection of an obstruction, such as, but not limited to, the movement of one or more components of person support apparatus 20. For example, in at least one embodiment, the shape and/or boundaries of a zone change based upon whether or not a siderail is in the up position or the down position. If a siderail is in an up position, it is less likely that an occupant of person support apparatus 20 will exit therefrom by climbing over that siderail. Accordingly, controller 58 may use, in that situation, a zone that allows the occupant's center of gravity to approach more closely to the up siderail than if the siderail were in a down position before issuing an alarm. If the siderail is moved to a lower position, the zone is switched to include a more restricted boundary—the more restricted boundary representing the fact that, with the siderail lowered, it is easier for an occupant to exit support deck 30 in the area of the lowered siderail. One manner of using siderail sensors to make an adjustment to an alert zone of an exit detection system is disclosed in commonly assigned U.S. Patent Application Publication No. 2017/0098359 to Sidhu et al., entitled PERSON SUPPORT APPARATUS WITH EXIT DETECTION SYSTEMS, the complete disclosure of which is incorporated herein by reference. Several other manners of adjusting the size, shape, and/or location of an alert zone are disclosed in U.S. patent application Ser. No. 16/917,004, filed Jun. 30, 2020 to Sukumaran, entitled PERSON SUPPORT APPARATUS WITH ADJUSTABLE EXIT DETECTION ZONES, which is also herein incorporated by reference in its entirety. In any of the embodiments where exit detection system 56 is configured to dynamically change the size, shape, and/or location of alert zones 98 based on the movement of one or more components, those changes are separate from and in addition to any changes it may make to the size, shape, and/or location of alert zones 98 based on the detection of contact with an obstruction.

Still further, it will also be understood that algorithm 1200, 1300, and/or 1400 may be modified in a number of manners from what is illustrated in FIGS. 11, 12, and 13, respectively. For example, any of these algorithms may be modified such that controller 58 does not utilize any compensation factors for events that don't involve contact with an obstruction. In other words, in any of algorithms 1200, 1300, and/or 1440, steps 1208, 1216, 1218, and 1220 (and their counterpart steps in algorithms 1300 and 1400) may be omitted. In such embodiments, controller 58 will not, for example, make any adjustments to the operation of exit detection system 58 if the calculated center of gravity changes due to movement of one or more components of person support apparatus 20 (e.g. the Fowler section 42 of support deck 30 pivots). In any of these embodiments where no compensation factors are used for movement that does not involve contact with an obstruction, exit detection system 56 may be configured to alternatively make adjustments to the size, shape, and/or location of the alert zones 98, or it may be configured to neither utilize a compensation factor nor a size, shape, and/or location change of zones 98. Still other modifications may be made.

It will also be understood that, although not illustrated in any of FIG. 11, 12, or 13, controller 58 is configured to repetitively take new load cell (e.g. force sensor 60) readings (such as, but not limited to, multiple times a second). These new load cell readings are used each time controller 58 returns to step 1210, 1310, or 1410 and calculates the occupant's current center of gravity. This current center of gravity is then compared in these steps to the alert zone 98 (or 198) and, if outside, an alert is issued (and if not, no alert is issued).

As was noted previously, exit detection system 56 can be modified from the embodiment shown in FIG. 4 and described herein to include a different number of sensors 66 and/or to compute a different number of compensation factors. Thus, in one example, exit detection system 56 is modified to not use any readings from any of the sensors 66*a-f*, while in other embodiments, controller 58 uses any one or more of the readings from sensors 66*a-f* to calculate compensation factors.

As was noted earlier, although FIGS. 14C and 15C illustrate only a single alert zone 98 (not counting the shifted alert zone 198), it will be understood that, in some embodiments, controller 58 changes the size, shape, and/or location of multiple zones in response to the detection of an obstacle.

It will also be understood that exit detection system 56 may be modified in still additional manners. For example, in some embodiments, exit detection system 56 may be modified to account for changes in the calculated center of gravity of the occupant that are due to the addition or subtraction of an object from litter frame 28. In such embodiments, controller 58 determines the position of the added or removed object in coordinate frame of reference 86, as well as the weight of the added or removed object, and mathematically calculates a compensation factor that accounts for this added or removed weight. The detection of an added or removed object, as well as the location of its addition or removal, can be accomplished in multiple different manners. In one manner, the addition or removal of an object is detected in the manner disclosed in commonly assigned U.S. patent application Ser. No. 62/065,242 filed Oct. 17, 2014 by inventors Marko N. Kostic et al. and entitled PERSON SUPPORT APPARATUS WITH MOTION MONITORING, the complete disclosure of which is incorporated herein by reference. The detection of an added or removed object may alternatively or additionally be determined by an image detection system such as that disclosed in commonly assigned U.S. patent application Ser. No. 13/242,022 filed Sep. 23, 2011 by inventors Richard Derenne et al. and entitled VIDEO MONITORING SYSTEM, the complete disclosure of which is also incorporated herein by reference. The detection and/or removal of an object can still further be determined by one or more thermal image sensors, such as those disclosed in commonly assigned U.S. patent application Ser. No. 61/989,243 filed May 6, 2014 by inventors Marko N. Kostic et al. and entitled PERSON SUPPORT APPARATUS WITH POSITION MONITORING, the complete disclosure of which is also incorporated herein by reference. Exit detection system 56 can therefore utilize and/or combine any of algorithms 1200, 1300, and/or 1440, or any of their modifications, with any of the features and/or algorithms of the systems disclosed in the aforementioned 62/065,242; 13/232,22; and/or 61/989,243 patent applications.

It will be understood by those skilled in the art that exit detection system 56 may also be modified to calculate an additional correction factor that is applied when force sensors 60 are implemented as load cells that are only capable of detecting vertical forces applied against them. Correction of such load cell readings is accomplished by multiplying the outputs of the load cells by a known trigonometric factor, as described in more detail in column 17, line 25 through column 21, line 30 of commonly assigned U.S. Pat. No. 7,702,481 entitled DIAGNOSTIC AND CONTROL SYSTEM FOR A PATIENT SUPPORT, the complete disclosure of which is also hereby incorporated herein by reference.

It will also be understood that, although exit detection system 56 has been primarily described herein as calculating a center of gravity of the occupant and issuing an alert when that center of gravity extends outside of an alert zone, exit detection system 56 can be configured to operate in manners that do not require the calculation of the occupant's center of gravity. For example, in some embodiments, exit detection system 56 can be configured to examine the ratios of the forces exerted on the head end, foot end, right side, and left side of the litter frame 28 and, if those ratios exceed a threshold, issue an exit alert. For example, if a total weight on litter frame 28 is equal to X, controller 58 may be programmed to issue an alert if more than, say, sixty-percent of X is distributed amongst the two left load cells (or amongst the two right load cells). In this manner, controller 58 doesn't need to explicitly calculate a center of gravity of the occupant, but instead can issue exit alerts when the weight supported on litter frame 28 shifts by more than a threshold amount toward either side (and/or toward head end 38 or foot end 40). In such embodiments, controller 58 can implement steps 1430 and 1434 of algorithm 1400 by changing the threshold that it uses to trigger an exit alert (e.g. instead of, say, sixty percent of the weight being supported on one side, it might use seventy percent). Still other manners of implementing steps 1430 and 1434 are possible.

Various alterations and changes can be made to the above description without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A person support apparatus comprising:

a litter frame;

a lift system adapted to raise and lower a height of the litter frame;

a support deck supported on the litter frame and adapted to support thereon an occupant of the person support apparatus;

an obstruction sensor adapted to detect when the litter frame contacts an obstruction during movement of the litter frame;

an exit detection system adapted to be in an armed state and a disarmed state, the exit detection system adapted to issue an exit alert in response to the occupant of the person support apparatus moving toward exiting the person support apparatus when the exit detection system is in the armed state, and to not issue the exit alert in response to an occupant of the person support apparatus moving toward exiting the person support apparatus when the exit detection system is in the disarmed state, the exit detection system comprising a plurality of force sensors adapted to output signals corresponding to downward forces exerted on the litter frame; and a controller in communication with the plurality of force sensors, the exit detection system, and the obstruction sensor, the controller adapted to automatically switch the exit detection system from the armed state to the disarmed state in response to the obstruction sensor detecting contact with an obstruction.

2. The person support apparatus of claim 1 wherein the controller is further adapted to automatically send a notification to a remote server in response to detecting the contact with the obstruction, the notification indicating that the controller has switched the exit detection system to the disarmed state.

3. The person support apparatus of claim 1 wherein the controller is further adapted to automatically switch the exit detection system back to the armed state from the disarmed state in response to the obstruction sensor no longer detecting contact with the obstruction.

4. The person support apparatus of claim 1 wherein the obstruction sensor is attached to an underside of the litter frame.

5. The person support apparatus of claim 1 wherein the exit detection system is adapted, when in the armed state, to calculate a center of gravity of the occupant, to compare the calculated center of gravity of the occupant to a boundary of a zone, and to issue the exit alert if the calculated center of gravity its outside of the boundary of the zone.

6. The person support apparatus of claim 5 wherein the controller is further adapted change at least one of a size, shape, or location of the zone in response to movement of a component of the person support apparatus.

7. The person support apparatus of claim 1 further comprising a second obstruction sensor, wherein the controller is adapted to automatically switch the exit detection system from the armed state to the disarmed state in response to either the obstruction sensor or the second obstruction sensor detecting contact with an obstruction.

8. A person support apparatus comprising:

a litter frame;

a lift system adapted to raise and lower a height of the litter frame;

a support deck supported on the litter frame and adapted to support thereon an occupant of the person support apparatus;

an obstruction sensor adapted to detect when the litter frame contacts an obstruction during movement of the litter frame;

an exit detection system adapted to be in an armed state and a disarmed state, the exit detection system adapted to issue an exit alert in response to the occupant of the person support apparatus moving toward exiting the person support apparatus when the exit detection system is in the armed state, and to not issue the exit alert in response to an occupant of the person support apparatus moving toward exiting the person support apparatus when the exit detection system is in the disarmed state, the exit detection system comprising a plurality of force sensors adapted to output signals corresponding to downward forces exerted on the litter frame; and a controller in communication with the plurality of force sensors, the exit detection system, and the obstruction sensor, the controller adapted to automatically issue the exit alert in response to the obstruction sensor detecting contact with an obstruction when the exit detection system is in the armed state, the controller further adapted to issue an obstruction alert in response to the obstruction sensor detecting contact with the obstruction when the exit detection system is in the disarmed state.

9. The person support apparatus of claim 8 wherein the controller is further adapted to not issue the exit alert in response to the obstruction sensor detecting contact with the obstruction when the exit detection system in is the disarmed state.

10. The person support apparatus of claim 8 wherein the controller is further adapted to automatically terminate the exit alert in response to the obstruction sensor no longer detecting contact with the obstruction.

11. The person support apparatus of claim 8 further comprising a second obstruction sensor adapted to detect when the litter frame contacts an obstruction during movement of the litter frame; wherein the controller is adapted to automatically issue the exit alert in response to either the obstruction sensor or the second obstruction sensor detecting contact with an obstruction when the exit detection system is in the armed state.

12. A person support apparatus comprising:

a litter frame;

a lift system adapted to raise and lower a height of the litter frame;

a support deck supported on the litter frame and adapted to support thereon an occupant of the person support apparatus;

an obstruction sensor adapted to detect when the litter frame contacts an obstruction during movement of the litter frame;

an exit detection system adapted to be in an armed state and a disarmed state, the exit detection system adapted to issue an exit alert in response to the occupant of the person support apparatus moving toward exiting the person support apparatus when the exit detection system is in the armed state, and to not issue the exit alert in response to an occupant of the person support apparatus moving toward exiting the person support apparatus when the exit detection system is in the disarmed state, the exit detection system comprising a plurality of force sensors adapted to output signals corresponding to downward forces exerted on the litter frame; and a controller in communication with the plurality of force sensors, the exit detection system, and the obstruction sensor, the controller adapted to automatically change operation of the exit detection system in a first manner in response to the obstruction sensor detecting contact with an obstruction when the exit detection system is in the armed state, wherein the first manner includes switching the exit detection system from operating at a first sensitivity level to a second and different sensitivity level.

13. The person support apparatus of claim 12 wherein the second sensitivity level is less sensitive than the first sensitivity level such that, when operating with the second sensitivity level, the occupant needs to move closer to an edge of the person support apparatus to trigger the exit alert than the occupant needs to move to trigger the exit alert when operating with the first sensitivity level.

14. The person support apparatus of claim 12 wherein the obstruction sensor is attached to an underside of the litter frame.

15. The person support apparatus of claim 12 wherein the exit detection system is adapted, when in the armed state, to calculate a center of gravity of the occupant, to compare the calculated center of gravity of the occupant to a boundary of a zone, and to issue the exit alert if the calculated center of gravity its outside of the boundary of the zone; and wherein the controller is adapted to change the operation of the exit detection system in the first manner by changing at least one of a size, shape, or position of the zone.

16. The person support apparatus of claim 12 wherein the exit detection system is adapted, when in the armed state, to calculate a center of gravity of the occupant, to compare the calculated center of gravity of the occupant to a boundary of a zone, and to issue the exit alert if the calculated center of gravity its outside of the boundary of the zone; and wherein the controller is adapted to change the operation of the exit detection system in the first manner by adjusting the calculated center of gravity in a manner that compensates for changes in the signals of the force sensors that are due to contact with the obstruction.

17. The person support apparatus of claim 12 wherein the obstruction sensor is adapted to detect when a first portion of the litter frame contacts the obstruction during movement of the litter frame, and further comprising a second obstruction sensor adapted to detect when a second portion of the litter frame different from the first portion contacts an obstruction during movement of the litter frame.

18. The person support apparatus of claim 17 wherein the controller is adapted to automatically change operation of the exit detection system in a second manner different from the first manner in response to the second obstruction sensor detecting contact with the obstruction when the exit detection system is in the armed state.

19. The person support apparatus of claim 18 wherein the exit detection system is adapted, when in the armed state, to perform the following: (1) calculate a center of gravity of the occupant, (2) compare the calculated center of gravity of the occupant to a boundary of a zone having a first size, a first shape, and a first location, and (3) to issue the exit alert if the calculated center of gravity its outside of the boundary of the zone; and wherein the controller is adapted to change the operation of the exit detection system in the first manner by changing at least one of the first size, first shape, or first position of the zone to a second size, a second shape, or a second position, respectively; and wherein the controller is further adapted to change the operation of the exit detection system in the second manner by changing at least one of the first size, first shape, or first position of the zone to a third size, a third shape, or a third position, respectively.

* * * * *